(12) United States Patent
Olson et al.

(10) Patent No.: US 8,500,797 B2
(45) Date of Patent: Aug. 6, 2013

(54) MEDICAL DEVICES

(75) Inventors: Greg Olson, Elk River, MN (US); Michael S. Arney, Minneapolis, MN (US); Scott R. Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 971 days.

(21) Appl. No.: 12/119,885

(22) Filed: May 13, 2008

(65) Prior Publication Data

US 2009/0012610 A1 Jan. 8, 2009

Related U.S. Application Data

(63) Continuation-in-part of application No. 10/936,042, filed on Sep. 8, 2004, now Pat. No. 7,722,578.

(51) Int. Cl.
  *A61F 2/06* (2006.01)
(52) U.S. Cl.
  USPC ........................................... 623/1.42
(58) Field of Classification Search
  USPC ................... 623/1.11, 1.46, 1.44, 1.42, 1.25, 623/1.12; 427/2.1, 566; 428/34.1, 36.1, 428/105, 111; 606/21, 23, 194, 27; 604/528, 604/103.06, 523, 103; 264/512
  See application file for complete search history.

(56) References Cited

U.S. PATENT DOCUMENTS

| | | | |
|---|---|---|---|
| 3,752,617 A | 8/1973 | Burlis et al. | |
| 4,782,834 A | 11/1988 | Maguire et al. | |
| 4,963,313 A | 10/1990 | Noddin et al. | |
| 5,195,969 A | 3/1993 | Wang et al. | |
| 5,248,305 A | 9/1993 | Zdrahala | |
| 5,270,086 A | 12/1993 | Hamlin | |
| 5,533,985 A | 7/1996 | Wang | |
| 5,622,665 A | 4/1997 | Wang | |
| 5,695,789 A | 12/1997 | Harris | |
| 5,714,110 A | 2/1998 | Wang et al. | |
| 5,728,079 A | 3/1998 | Weber et al. | |
| 5,797,877 A | 8/1998 | Hamilton et al. | |
| 5,817,017 A | 10/1998 | Young et al. | |

(Continued)

FOREIGN PATENT DOCUMENTS

| | | |
|---|---|---|
| EP | 0775500 | 5/1997 |
| EP | 1344549 | 9/2003 |

(Continued)

OTHER PUBLICATIONS

Choi, E.S. et al., "Enhancement of Thermal and Electrical Properties of Carbon Nanotube polymer Composites by Magnetic Field Processing," Journal of Applied Physics, vol. 94, No. 9, Nov. 1, 2003, 6035-6039.

(Continued)

*Primary Examiner* — Thomas J Sweet
*Assistant Examiner* — Matthew Schall
(74) *Attorney, Agent, or Firm* — Seager, Tufte & Wickhem, LLC

(57) ABSTRACT

Medical devices and related methods are disclosed. In some embodiments, a method of manufacturing a medical device or a medical device component includes contacting a non-fluid first member and a second member, the first member comprising a first polymer and an alignable material different from the first polymer; aligning the alignable material; and bonding the first and second members together.

20 Claims, 15 Drawing Sheets

(56) References Cited

U.S. PATENT DOCUMENTS

| | | | |
|---|---|---|---|
| 5,951,494 | A | 9/1999 | Wang et al. |
| 6,120,364 | A | 9/2000 | Laflamme |
| 6,173,199 | B1 | 1/2001 | Gabriel |
| 6,436,056 | B1 | 8/2002 | Wang et al. |
| 6,726,712 | B1 | 4/2004 | Raeder-Devens et al. |
| 6,790,425 | B1 | 9/2004 | Smalley et al. |
| 6,864,418 | B2 | 3/2005 | Wang et al. |
| 6,946,092 | B1 | 9/2005 | Bertolino et al. |
| 7,029,495 | B2 * | 4/2006 | Stinson ................ 623/1.32 |
| 7,163,655 | B2 * | 1/2007 | Weber et al. ............ 264/474 |
| 7,458,798 | B2 * | 12/2008 | Weber et al. .......... 425/378.1 |
| 2002/0165523 | A1 | 11/2002 | Chin et al. |
| 2003/0055449 | A1 | 3/2003 | Lee et al. |
| 2003/0093107 | A1 | 5/2003 | Parsonage et al. |
| 2003/0100830 | A1 | 5/2003 | Zhong et al. |
| 2003/0163148 | A1 | 8/2003 | Wang et al. |
| 2003/0183986 | A1 | 10/2003 | Weber |
| 2004/0021249 | A1 | 2/2004 | Weber et al. |
| 2004/0044397 | A1 * | 3/2004 | Stinson ................ 623/1.15 |
| 2004/0078052 | A1 | 4/2004 | St. Pierre et al. |
| 2004/0167506 | A1 | 8/2004 | Chen |
| 2004/0210211 | A1 | 10/2004 | Devens, Jr. et al. |
| 2005/0043679 | A1 | 2/2005 | Devens et al. |
| 2005/0043712 | A1 | 2/2005 | Devens, Jr. et al. |
| 2005/0119616 | A1 * | 6/2005 | Goodin et al. ............ 604/103 |
| 2005/0149102 | A1 | 7/2005 | Radisch, Jr. et al. |
| 2005/0163954 | A1 | 7/2005 | Shaw |
| 2005/0251107 | A1 | 11/2005 | Olson |
| 2005/0260355 | A1 | 11/2005 | Weber et al. |
| 2005/0261670 | A1 | 11/2005 | Weber et al. |
| 2006/0051535 | A1 | 3/2006 | Arney et al. |
| 2007/0102848 | A1 * | 5/2007 | Weber et al. ............ 264/474 |
| 2008/0160259 | A1 * | 7/2008 | Nielson et al. ............ 428/148 |

FOREIGN PATENT DOCUMENTS

| | | |
|---|---|---|
| EP | 1388346 | 2/2004 |
| WO | 9518674 A2 | 7/1995 |
| WO | 0132398 | 5/2001 |
| WO | 2005056097 A1 | 6/2005 |
| WO | 2005112845 A1 | 12/2005 |
| WO | 2006029136 A1 | 3/2006 |

OTHER PUBLICATIONS

Cutillas, S. and Liu, J., "Dynamics of Single Chains of Suspended Ferrofluid Particles," presented at the Fourth Microgravity Fluid Physics and Transport Phenomena Conference (Aug. 12-14, 1998, Cleveland, Ohio), pp. 100-105.

Garmestani, H., "Polymer-Mediated Alignment of Carbon Nanotubes Under High Magnetic Fields." Adv. Mater. 15, No. 22, Nov. 17, 2003, 1918-1921.

Guo, Y. et al., "Manipulation of Single-Wall Carbon Nanotubes into Aligned Molecular Layers", Chemical Physics Letters 362 (2002), 314-318.

Guo, Y. et. al., "Multi-layer LB Films of Single-Wall Carbon Nanotubes", Physica B 323 (2002), 235-236.

HandsOn 15—The Hele-Shaw Experiment with Glycerin (4 pages) Available Web Site: http://polymer.bu.edu/ogaf/html/chp44expl.htm (Retrieved from the Internet prior to the filing of the application.).

"Magnets Align Nanotubes in Resin", Apr. 21/28, 2004 Available Web Site: http://trnmag.com/Stories/2004/042104/Magnets_align_nanotubes_in_resin_brief 042104.

Prasse, T. et al., "Electric Anisotropy of Carbon Manofibre/Epoxy Resin Composites Due to Electric Field Induced Alignment", Composites Science and Technology 63 (2003), 1835-1841.

Walker, J., "How to Build a Hele-Shaw Cell," Scientific American's The Amateur Scientist, Oct. 1989 (2 pages) Available Web Site: www.sas.org/E-Bulletin/2003-09-12/abNotesAS/body.html.

* cited by examiner

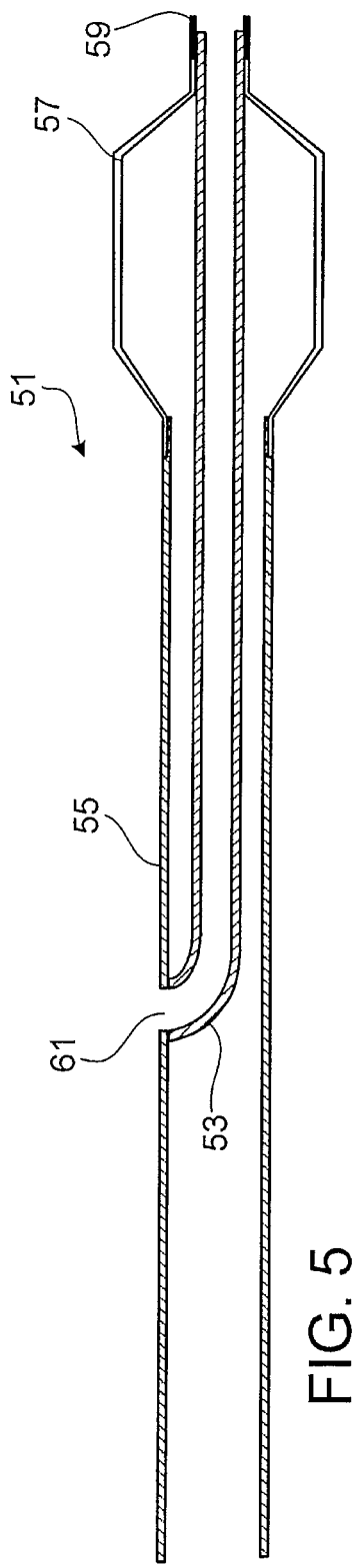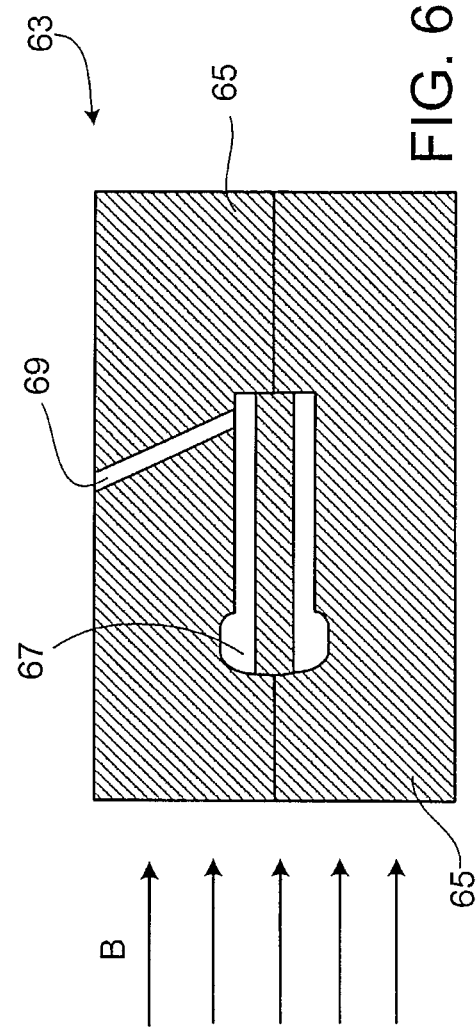

MEDICAL DEVICES

RELATED APPLICATIONS

This application is a continuation-in-part of and claims priority to U.S. patent application Ser. No. 10/936,042, filed on Sep. 8, 2004, which published as U.S. Patent Application Publication No. US 2006/0051535 A1 on Mar. 9, 2006, and which is incorporated herein by reference in its entirety.

TECHNICAL FIELD

The invention relates to medical devices (e.g., medical tubing, guide wires, catheters, balloon catheters, stent-grafts, stents), and to related methods.

BACKGROUND

Intravascular medical devices such as, for example, guide wires, catheters, and medical tubing, allow physicians to perform a medical procedure, such as balloon angioplasty (e.g., percutaneous transluminal coronary angioplasty) or delivery of an endoprosthesis (e.g., a stent). In some cases, a device is inserted into a patient's vascular system at a convenient site and subsequently delivered (e.g., pushed) through the vascular system to a target site. The path that the device takes through the vascular system to the target site can be relatively tortuous, for example, requiring the device to change direction frequently.

In some circumstances, it is desirable for the device to have relatively good flexibility so that it can track along the tortuous path. At the same time, the device preferably has good pushability so that forces applied proximally to the device can be transmitted distally to deliver the device.

SUMMARY

The invention relates to medical devices.

In one aspect, the invention features a method of manufacturing a medical device or a medical device component, the method including extruding a first polymer that includes a magnetically alignable material, and applying a magnetic field to the magnetically alignable material as the first polymer is extruded in a liquid state. The method also includes solidifying the first polymer to form the medical device or the medical device component.

In another aspect, the invention features a method of making a medical device or a medical device component, the method including orienting a first magnetically alignable material in a first composition that is in a liquid state and that includes a first polymer and the first magnetically alignable material. The method also includes solidifying the first composition to form the medical device or the medical device component.

In an additional aspect, the invention features a medical device with a first portion including a first magnetically alignable material that is oriented in one direction. The medical device also has a second portion including a second magnetically alignable material that is not oriented in the same direction as the first magnetically alignable material.

In a further aspect, the invention features a medical device with a first portion including magnetically alignable fibers that have a non-random orientation within the first portion, and a second portion that is adjacent to the first portion.

In another aspect, the invention features a medical device with a tubular member including magnetically alignable fibers. The magnetic permeability of a first portion of the tubular member is different from the magnetic permeability of a second portion of the tubular member.

In an additional aspect, the invention features a medical device with a first portion and a second portion. The first portion includes magnetically alignable particles that are collectively oriented in a first direction, and the second portion includes magnetically alignable particles that are not collectively oriented in the first direction.

Embodiments can include one or more of the following features.

The method can further include varying the magnetic field strength of the magnetic field. In some embodiments, the magnetic field can have a magnetic field strength of up to about 30 Tesla. In certain embodiments, the magnetic field can have a magnetic field strength of from about 25 gauss to about 600 gauss. Applying a magnetic field to the magnetically alignable material can include exposing the magnetically alignable material to a solenoid. Applying a magnetic field to the first polymer can include extruding the first polymer over a magnetic mandrel.

The method can further include extruding (e.g., intermittently extruding, continuously extruding) the first composition to form a member.

The medical device or the medical device component can be a catheter, a guide wire, a balloon, or an endoprosthesis delivery system. In embodiments in which the medical device or medical device component is a balloon, the balloon can include one or more cutting elements. The medical device or the medical device component can have a first portion and a second portion with different flexibilities and/or different magnetic permeabilities. The first portion and/or the second portion can have a magnetic permeability of from about one to about 20 or from about five to about 30. The medical device or the medical device component can have a first portion including the magnetically alignable material, and a second portion that is substantially free of the magnetically alignable material. The distal end of the medical device or the medical device component can be more flexible than the proximal end. The first portion and/or second portion of the medical device or medical device component can be a layer or section of the medical device or medical device component.

The magnetically alignable material can be in the form of particles (e.g., spherical particles). The particles can have an average length of from about 50 nanometers to about 25 microns. The particles can have an average width or diameter of from about five nanometers to about 25 microns (e.g., from about 50 nanometers to about 25 microns). The method can further include orienting the particles in a first portion of the medical device or the medical device component to have a first orientation, and orienting the particles in a second portion of the medical device or the medical device component to have a second orientation that is different from the first orientation. The method can include orienting the particles in the first portion of the medical device or the medical device component to have an orientation that is parallel or lateral to the longitudinal axis of the medical device or the medical device component. The method can include orienting the particles in the second portion of the medical device or the medical device component to have a random orientation.

The magnetically alignable material can include one or more nanomaterials.

The concentration of the magnetically alignable material in the first polymer can be from about two weight percent to about 50 weight percent. The magnetically alignable material can include a ferromagnetic material. The first polymer can include a magnetorheological fluid including the magnetically alignable material.

The magnetically alignable material can be in the form of fibers. The fibers can have an average aspect ratio of from about one to about 25. The fibers can have an average length of from about 50 nanometers to about 25 microns, and/or an average width of from about five nanometers to about 25 microns.

Orienting the first magnetically alignable material can include varying the orientation of the first magnetically alignable material. Orienting the first magnetically alignable material can include orienting the first polymer.

The method can further include coextruding (e.g., simultaneously or sequentially) a second polymer (e.g., as a layer) to form the medical device or the medical device component. The first polymer can be different from the second polymer. The second polymer can be substantially free of magnetically alignable material.

The method can further include varying the thickness of the first composition and/or the second composition in the member. The method can further include coextruding (e.g., intermittently coextruding, continuously coextruding) a second composition in a liquid state with the first composition to form the member. The second composition can include a second polymer and a second magnetically alignable material. The method can further include orienting the second magnetically alignable material in the second composition (e.g., so that the second magnetically alignable material has an orientation that is different from the orientation of the first magnetically alignable material). The first magnetically alignable material and the second magnetically alignable material can be the same. The second magnetically alignable material can be randomly oriented. The second magnetically alignable material can be partially aligned relative to the first direction.

The second portion can be substantially free of magnetically alignable material. The second portion can be attached to the first portion. The second portion can be integrally formed with the first portion. The first portion can include a first polymer and the second portion can include a second polymer that is different from the first polymer. The first portion and the second portion can be coextruded. The first portion can include the magnetically alignable fibers and the second portion can be substantially free of the magnetically alignable fibers.

The magnetically alignable particles can form at least one line that is oriented in the first direction. The magnetically alignable particles can be randomly oriented.

The tubular member can consist essentially of a single composition. The tubular member can have just one layer or more than one layer. The tubular member can have a first layer that includes the magnetically alignable fibers, and a second layer that is substantially free of the magnetically alignable fibers.

Embodiments can have one or more of the following advantages.

In some embodiments, a medical device (e.g., a catheter) that includes magnetically alignable material can exhibit variable stiffness. For example, the proximal end of the medical device can be relatively stiff, while the distal end of the medical device can be relatively flexible. The relatively stiff proximal end can enhance the pushability of the medical device, such that the medical device can be easily pushed into the body of a patient (e.g., without kinking or buckling). The relatively flexible end of the medical device can enhance the trackability of the medical device, such that the medical device can be easily directed within the body of the patient. In certain embodiments, the medical device that exhibits variable stiffness can be formed by continuously extruding a polymer that includes magnetically alignable material embedded within it. A medical device that is formed of a continuously extruded polymer can exhibit enhanced mechanical integrity relative to a medical device that is formed of two or more different polymeric portions (e.g., that are butt welded to each other).

In one aspect, the invention features a method of manufacturing a medical device or a medical device component, the method including contacting a non-fluid first member and a second member, the first member comprising a first polymer and an alignable material different from the first polymer; aligning the alignable material; and bonding the first and second members together.

Embodiments can include one or more of the following features. The alignable material is aligned after contacting the first member and the second member. The alignable material is aligned magnetically. The alignable material includes carbon, such as a carbon nanotube or a carbon fiber. The first member includes from about 2 to about 50 percent by weight of the alignable material. The first and second members are held in contact by a heat shrink material. The first and second members are bonded by heating at least one of the members. The first and second members are bonded using a laser. The second member includes a second polymer and, optionally, a second alignable material. The first and second members are components of a balloon catheter.

In another aspect, the invention features a method of manufacturing a medical device or a medical device component, the method including introducing a first composition comprising a first polymer and an alignable material into a cavity; aligning the alignable material; and solidifying the first composition in the cavity.

Embodiments can include one or more of the following features. The alignable material is aligned magnetically. The alignable material includes carbon, such as a carbon nanotube or a carbon fiber. The first composition includes from about 2 to about 50 percent by weight of the alignable material. The first composition is solidified to form a component of a balloon catheter.

In another aspect, the invention features an endoprosthesis, the endoprosthesis including a metallic tubular structure; and a first composition on the tubular structure, the first composition includes a polymer and an alignable material comprising a carbon nanotube or a carbon fiber aligned along a selected direction.

Embodiments can include one or more of the following features. The first composition further includes a drug. The first composition includes from about 2 to about 50 percent by weight of the alignable material.

Other aspects, features and advantages of the invention will be apparent from the description of the preferred embodiments and from the claims.

DESCRIPTION OF DRAWINGS

FIG. 5 is a cross-sectional side view of an embodiment of a balloon catheter.

FIG. 6 is schematic of an embodiment of a method of making a medical device component.

DETAILED DESCRIPTION

Figure 1:
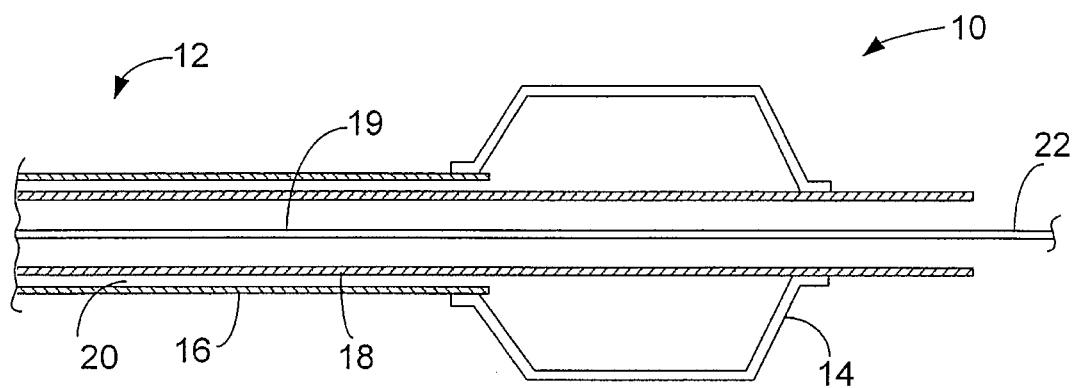
FIG. 1 is a cross-sectional side view of an embodiment of a balloon catheter.

Referring to FIG. 1, a balloon catheter system 10 includes a catheter 12 and an inflatable balloon 14 carried by the catheter. Catheter 12 includes an outer shaft 16 and an inner shaft 18 defining a lumen 19. Shafts 16 and 18 are concentric and define an annular lumen 20 between them. During use, catheter system 10 can be delivered to a treatment area (e.g., a coronary artery) by passing lumen 19 over a guide wire 22 emplaced in the body, and pushing the catheter system to the treatment area. Balloon 14 can then be inflated or deflated by delivering or withdrawing a fluid (such as a liquid or a gas) through annular lumen 20. Examples of balloon catheter systems are described in U.S. Pat. Nos. 5,195,969 and 5,270,086.

Figure 2:
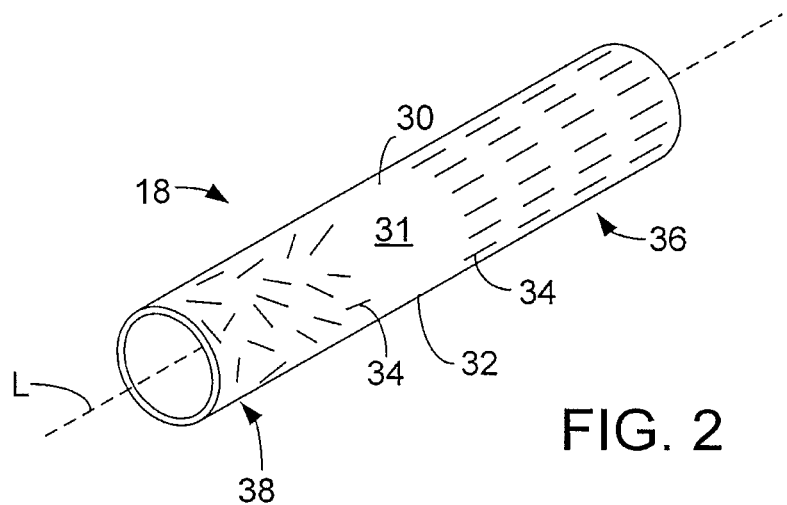
FIG. 2 is a perspective view of an embodiment of a tube for a balloon catheter system.

Referring now to FIG. 2, inner shaft 18 is tubular and is formed of a continuously extruded polymer composite layer 30 that includes a polymer matrix 32 and magnetically alignable fibers 34 embedded in the polymer matrix. Inner shaft 18 has a relatively stiff proximal end 36 and a relatively flexible distal end 38. The magnetically alignable fibers in proximal end 36 are oriented parallel to the longitudinal axis "L" of inner shaft 18, contributing to the relative stiffness of proximal end 36. The magnetically alignable fibers in proximal end 36 have a non-random orientation because they have all been oriented substantially in the same direction. The magnetically alignable fibers in distal end 38 are randomly oriented, contributing to the relative flexibility of distal end 38. The stiffness of proximal end 36 provides inner shaft 18 with good pushability, while the flexibility of distal end 38 provides inner shaft 18 with good trackability. As shown in FIG. 2, the intermediate region 31 of inner shaft 18 does not include any magnetically alignable fibers 34. However, in some embodiments (and as shown below), intermediate region 31 can include magnetically alignable fibers 34.

Figure 3A:
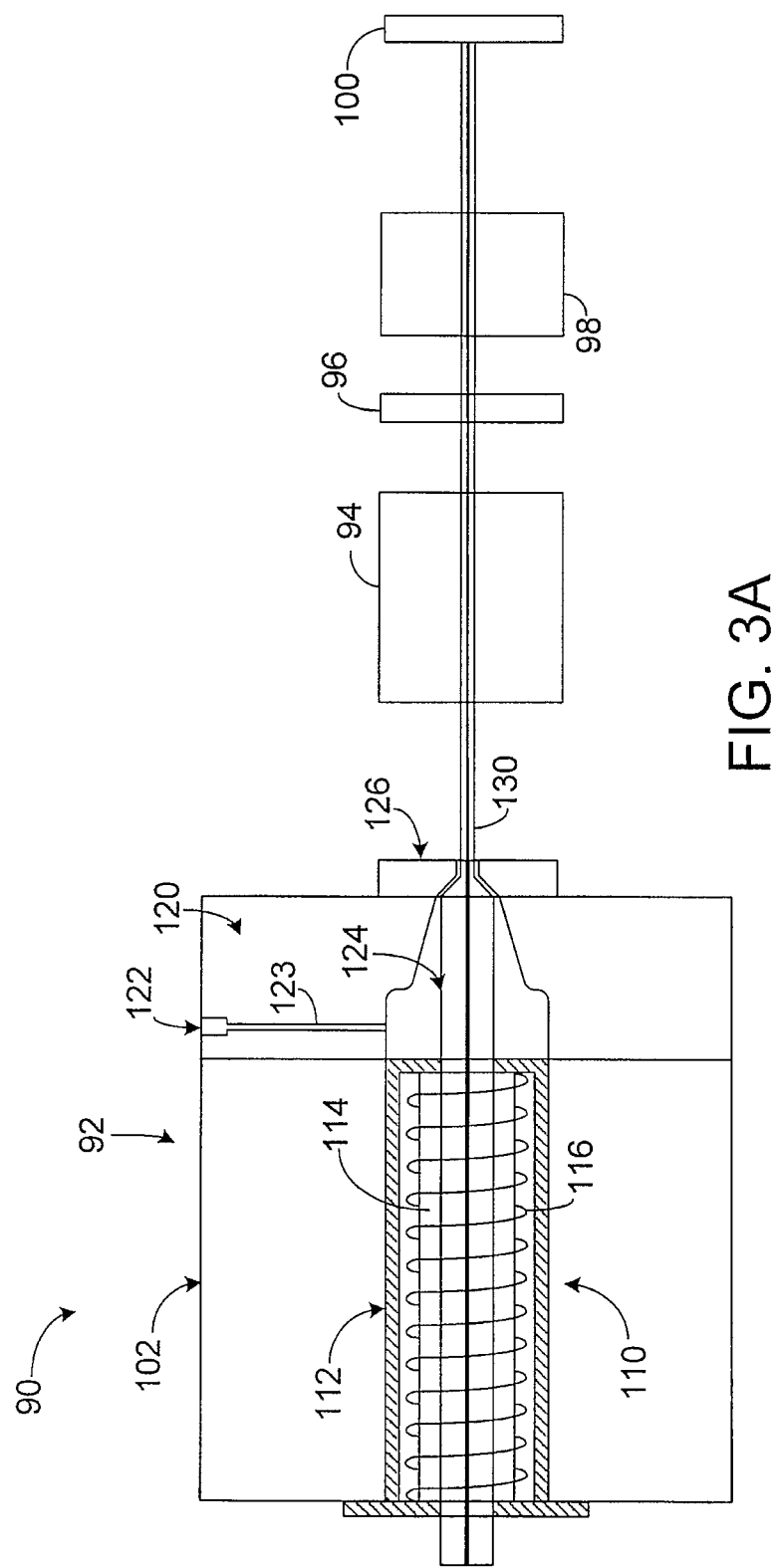
FIG. 3A is an illustration of an embodiment of an apparatus for making a tube for a balloon catheter system.

Referring to FIG. 3A, inner shaft 18 can be made, for example, using a tube-forming apparatus 90. Tube-forming apparatus 90 includes an extrusion head 92, a quench tank 94, a laser micrometer 96, a puller 98, and a cut-off knife 100. Extrusion head 92 includes a housing 102 that encloses three sections of the extrusion head: a magnetic field-generating section 110, a polymer feed section 120, and an extrusion die 126. Magnetic field-generating section 110 includes a steel sleeve 112, an iron tip guide 114, and a coil 116 (e.g., a solenoid) disposed between iron tip guide 114 and steel sleeve 112. Polymer feed section 120 includes a polymer feed 122 that, via a polymer feed shaft 123, is in fluid communication with a hollow tip 124 that extends through all three sections of extrusion head 92.

To form inner shaft 18, a polymer composite that includes a polymer matrix material and magnetically alignable fibers 34 is added into polymer feed 122. While it is in polymer feed 122, the polymer composite is melted to form a liquid polymer composite stream (e.g., a magnetorheological fluid) that flows through polymer feed shaft 123, and into tip 124, exiting extrusion head 92 through extrusion die 126. The polymer composite stream starts to solidify upon exiting extrusion head 92 through extrusion die 126, at which point the polymer composite stream is exposed to the ambient environment. As the polymer composite stream solidifies, it forms a tubular member 130. As the polymer composite is being extruded, pressurized air (shown in FIG. 3A as a solid black line) flows through the center of hollow tip 124. The pressurized air causes the polymer composite stream to form a tubular shape as it is extruded. As an alternative to pressurized air, in some embodiments, the polymer composite stream can be extruded over a mandrel (not shown) that causes the polymer composite stream to form a tubular shape when it is extruded. The mandrel can be formed of, for example, cast iron, carbon steel, or stainless steel (e.g., 306 stainless steel, 316 stainless steel, 440C stainless steel). After exiting extrusion die 126, tubular member 130 passes through quench tank 94, for further cooling and solidification. Thereafter, tubular member 130 passes through laser micrometer 96, where it is sized, and through puller 98, which pulls tubular member 130 from extrusion die 126, through quench tank 94 and laser micrometer 96, and directs tubular member 130 toward cut-off knife 100.

Figure 3B:
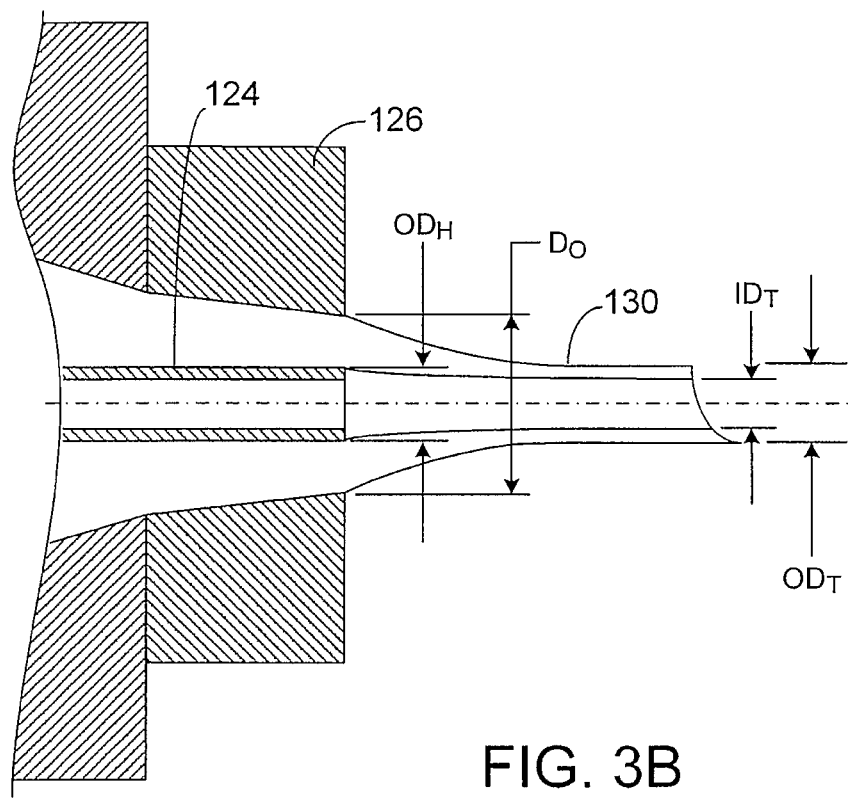
FIG. 3B is a side view of a portion of the apparatus of FIG. 3A.

Referring now to FIG. 3B, the orifice of extrusion die 126 has a diameter $D_O$, hollow tip 124 has an outer diameter $OD_H$, and tubular member 130 has an inner diameter $ID_T$ and an outer diameter $OD_T$. Operation of the puller 98 affects the draw-down ratio $[(D_O)/(OD_T)]$ and the draw-balance ratio $[((D_O)/(OD_T))/((OD_H)/(ID_T))]$ of tubular member 130. In embodiments, the draw-down ratio of tubular member 130 can be from about two to about 2.5. Alternatively or additionally, the draw-balance ratio of tubular member 130 can be from about 1.05 to about 1.1. Finally, tubular member 130 passes through cut-off knife 100, which cuts tubular member 130 into smaller pieces, such as inner shaft 18. Inner shaft 18 can then be incorporated into catheter system 10 by conventional methods. For example, inner shaft 18 can be attached to balloon 14 using an adhesive, laser welding, and/or RF welding.

Suitable operating conditions for tube-forming apparatus 90, such as zone heating temperatures, polymer concentrations, feed rate, and line speed, are described, for example, in Chin et al., U.S. Published Patent Application No. 2002/0165523 A1, which is incorporated herein by reference in its entirety.

Figure 3C:
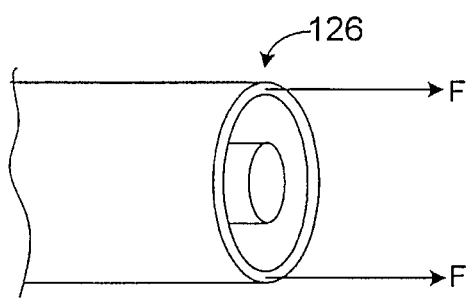
FIG. 3C is a perspective view of a portion of the apparatus of FIG. 3A, when exposed to a magnetic field.
Figure 3D:
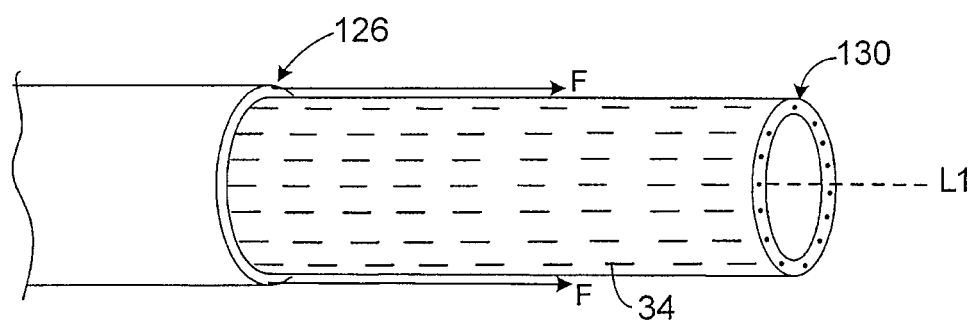
FIG. 3D is a perspective view of a portion of the apparatus of FIG. 3A, when extruding a material under exposure to a magnetic field.

During the extrusion process, a magnetic field is applied to the polymer composite stream to align the magnetically alignable material within the polymer composite stream. Referring to FIG. 3A, coil 116 is selectively activated (by passing electrical current through the coil) to align magnetically alignable fibers 34 within the polymer composite stream. As shown in FIG. 3C, when coil 116 is activated, it generates a magnetic field force in the direction of arrows F. Iron tip guide 114 propagates the magnetic field along the length of tip 124, from the location of coil 116 to extrusion die 126. Thus, the polymer composite stream is exposed to the magnetic field as the polymer composite stream flows through tip 124 and extrusion die 126. Exposure of the liquid polymer composite stream to the magnetic field can cause magnetically alignable fibers 34 to respond by aligning themselves with the field. As shown in FIG. 3D, when coil 116 is activated during the formation of tubular member 130, the resultant magnetic field causes magnetically alignable fibers 34 to become aligned parallel to the longitudinal axis "L1" of tubular member 130.

Figure 3E:
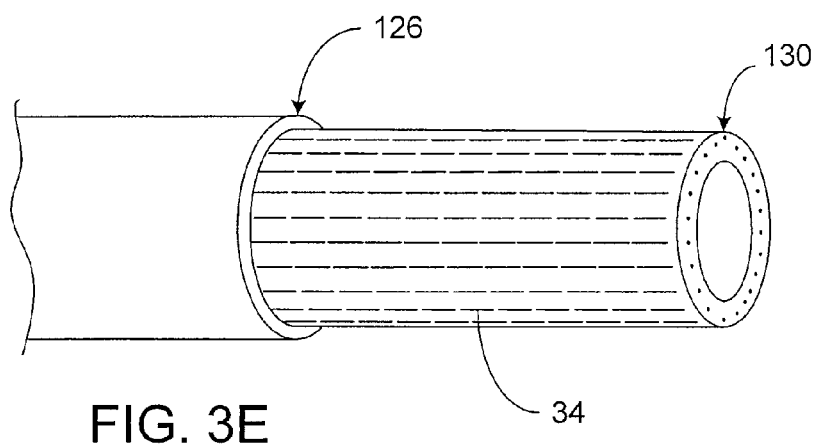
FIG. 3E is a perspective view of a portion of the apparatus of FIG. 3A, when extruding a material under exposure to a magnetic field.
Figure 3F:
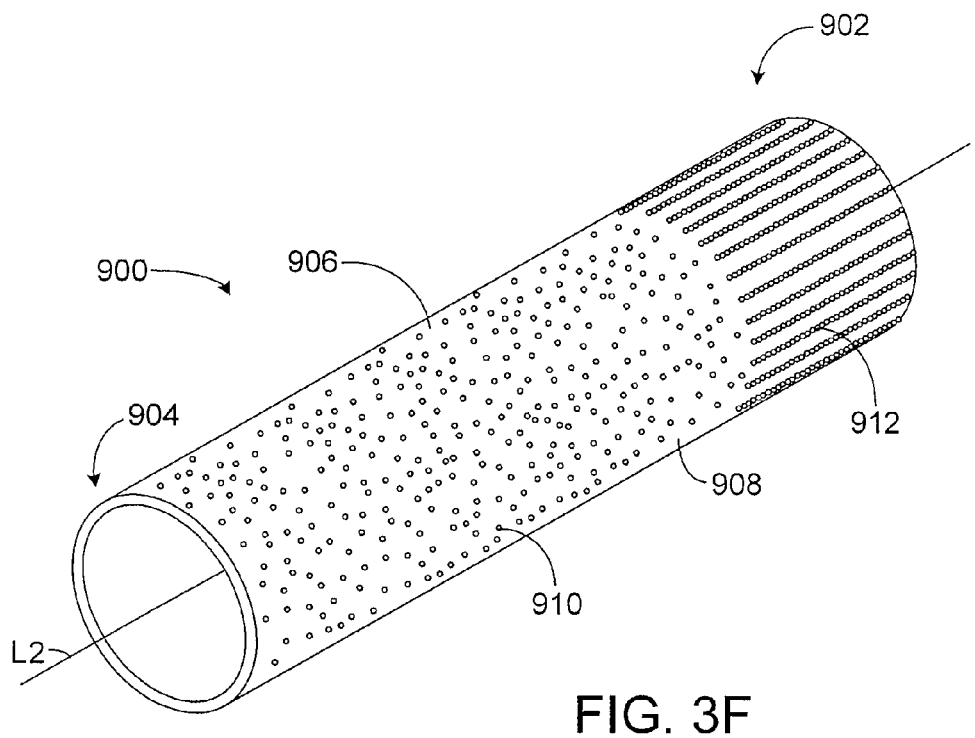
FIG. 3F is a perspective view of an embodiment of a tube for a balloon catheter system.

In some embodiments, and referring now to FIG. 3E, the resultant magnetic field can cause magnetically alignable fibers 34 to line up in a "train" formation. The train formation can occur as a result of a magnetic dipole being formed along the axis of each fiber 34. This magnetic dipole causes the fibers to join end-to-end (e.g., in close proximity, contacting), thereby forming a long, fibrous train of fibers 34. In certain embodiments, a train formation can be created using spherical magnetically alignable particles. For example, FIG. 3F shows a shaft 900 with a proximal end 902, a distal end 904, and a longitudinal axis "L2". Shaft 900 is tubular and is formed of a continuously extruded polymer composite layer 906 that includes a polymer matrix 908 and spherical magnetically alignable particles 910 embedded in the polymer matrix. While the magnetically alignable particles at distal end 904 are randomly dispersed throughout polymer matrix 908, the magnetically alignable particles at proximal end 902 have aligned so that they form long trains 912 of the particles. Trains 912, which are oriented parallel to longitudinal axis "L2" of shaft 900, cause proximal end 902 of shaft 900 to be relatively stiff. By contrast, distal end 904, with its randomly oriented particles, is relatively flexible. The formation of trains of magnetic particles is described, for example, in Cutillas & Liu, "Dynamics of Single Chains of Suspended Ferrofluid Particles," presented at the Fourth Microgravity Fluid Physics & Transport Phenomena Conference (Aug. 12-14, 1998, Cleveland, Ohio), pages 100-105, which is incorporated herein by reference.

Figure 3G:
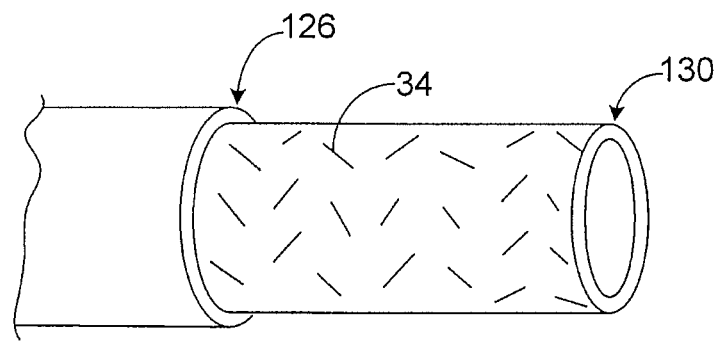
FIG. 3G is a perspective view of a portion of the apparatus of FIG. 3A, when extruding a material that is not under exposure to a magnetic field.

FIG. 3G shows that the deactivation of coil 116 results in magnetically alignable fibers 34 having a random orientation, since they are no longer exposed to a magnetic field. In some embodiments, activation or deactivation of coil 116 can affect the concentration of magnetically alignable fibers 34. For example, the magnetic field created by coil 116 can pull magnetically alignable fibers 34 through the liquid polymer composite as it is being extruded. When coil 116 is deactivated, this pulling force stops, such that magnetically alignable fibers 34 remain where they are in the polymer composite. Thus, a section of the extruded tube that was formed while coil 116 was activated may have a higher concentration of magnetically alignable fibers 34 than a section of the extruded tube that was formed while coil 116 was deactivated. A medical device component such as inner shaft 18 can be formed by activating coil 116 during one part of the extrusion process (e.g., during the formation of relatively stiff proximal end 36), and deactivating coil 116 during another part of the extrusion process (e.g., during the formation of relatively flexible distal end 38).

Figure 3H:
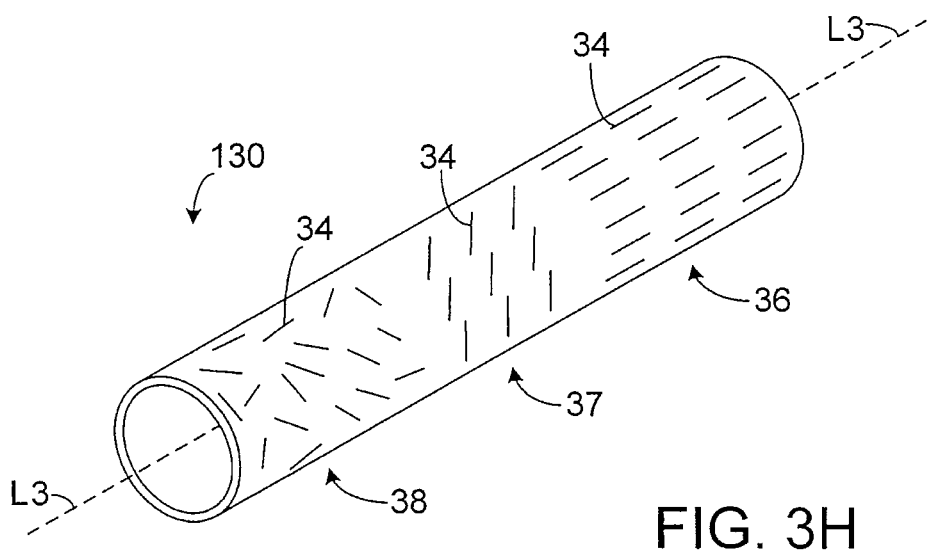
FIG. 3H is a perspective view of an embodiment of a tubular member.

In some embodiments, and referring now to FIG. 3H, tubular member 130 can be formed to have a relatively stiff proximal end 36, a relatively flexible distal end 38, and an intermediate region 37 with a flexibility between that of proximal end 36 and distal end 38. As shown, intermediate region 37 includes magnetically alignable fibers 34 that all have the same orientation relative to longitudinal axis "L3" of tubular member 130, but that are not aligned parallel to longitudinal axis "L3". Intermediate region 37 of tubular member 130 can be formed, for example, as coil 116 is deactivated. Prior to deactivation of coil 116, the magnetically alignable fibers 34 in intermediate region 37 begin to become aligned relative to longitudinal axis "L3". However, coil 116 is deactivated before the magnetically alignable fibers in the intermediate region can be aligned parallel to longitudinal axis "L3". Thus, the magnetically alignable fibers in the intermediate region are "partially aligned" relative to longitudinal axis "L3". Because intermediate region 37 includes magnetically alignable fibers with an intermediate alignment relative to the fibers in proximal end 36 and distal end 38, intermediate region 37 has an intermediate flexibility, as well.

The strength of the magnetic field (e.g., created by a coil such as coil 116) that is applied to magnetically alignable material can be selected based on the extent of alignment desired for the magnetically alignable material. In some instances, the strength of the magnetic field that is selected to induce a certain extent of alignment of the magnetically alignable material may depend on the type of polymer in which the magnetically alignable material is embedded, and/or on the size of the magnetically alignable material. For example, a magnetic field with a relatively high magnetic field strength may be used to align magnetically alignable material (e.g., fibers, particles) that is relatively small in size, and/or that is embedded in a polymer with a relatively high polymer melt viscosity. Another factor that may influence the strength of the magnetic field selected to align the magnetically alignable material is the magnetic permeability of the magnetically alignable material. As an example, in some embodiments, a magnetic field with a relatively high magnetic field strength can be used to align iron particles that have a diameter of about one micron and that are suspended in a molten 72 durometer Pebax matrix. As another example, in certain embodiments, a magnetic field with a relatively low magnetic field strength can be used to align iron particles that have a diameter of about ten microns and that are suspended in a low density polyethylene matrix. In some embodiments, the magnetic field (e.g., created by a coil such as coil 116) that is applied to magnetically alignable material can have a magnetic field strength of from about 25 gauss to about 600 gauss (e.g., from about 100 gauss to about 400 gauss).

While the above-described processes have been described with respect to inner shaft 18, in some embodiments, other components of balloon catheter system 10 can alternatively or additionally be formed as described above with respect to inner shaft 18. For example, outer shaft 16 can include magnetically alignable material having different orientations along the length of outer shaft 16. For example, balloon catheter 14 can include magnetically alignable material having different orientations along the length of the balloon.

In certain embodiments, a tubular component can be made with aligned magnetically alignable materials, and can later be connected (e.g., by welding) to a tubular component that does or does not include aligned magnetically alignable material, to form a tubular member.

For example, balloon 14 can be formed, for example, by a blow molding process in which the tubular member is placed (e.g., centered) in a preheated balloon mold, and air is introduced into the tube to maintain the patency of the tube lumen. In some embodiments, after being soaked at a predetermined temperature and time, the tube can be stretched for a predetermined distance at a predetermined time, rate, and temperature. The pressure inside the tube can then be sufficiently increased to radially expand the tube inside the mold to form the balloon. The formed balloon can be heat treated, for example, to enhance folding memory, and/or folded into a predetermined profile. Methods of forming a balloon from a tube are described in, for example, Bertolino, U.S. Pat. No. 6,946,092; Anderson, U.S. Pat. No. 6,120,364; Wang, U.S. Pat. No. 5,714,110; and Noddin, U.S. Pat. No. 4,963,313.

Figure 4:
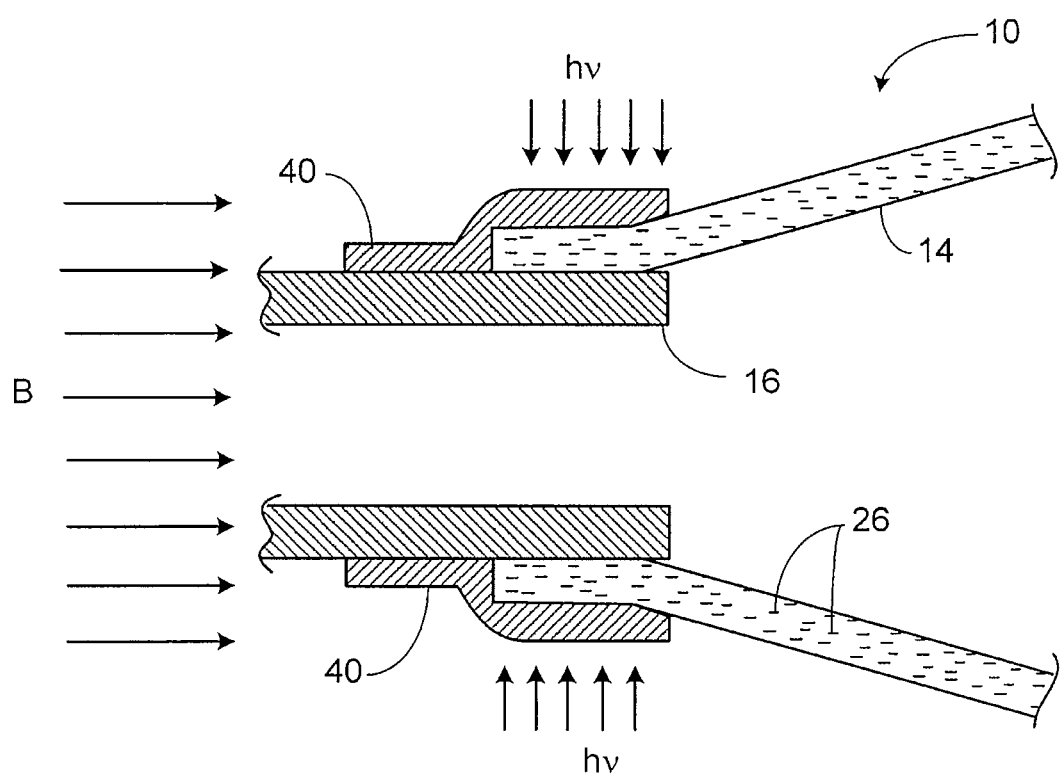
FIG. 4 is a detailed view of an embodiment of a method of making a balloon catheter.

After a balloon is formed, the balloon is secured to outer shaft 16. Referring to FIG. 4, balloon 14 including alignable material 26 is placed coaxially around outer shaft 16 and temporarily secured in place by placing a tube including a heat-shrink material 40 around the balloon and outer shaft and heating the tube. Examples of heat-shrink material 40 include polyesters, nylons, polyamides, polyethylene terephthalate (PET), polybutylene terephthalate (PBT), PET-based elastomers, PBT-based elastomers, thermoplastic polyurethanes, polyether block amide, polyolefins, polyvinyl chloride, fluoropolymers and mixtures thereof. Examples of fluoropolymers include fluorinated ethylene propylene copolymer (FEP), polyvinylidene difluoride (PVDF) and polytetrafluoroethylene (PTFE). Heat-shrink material 40 may include (e.g., be compounded with) non-stick additives, such as polytetrafluoroethylene (PTFE) powder (Dupont) and/or silicones (Dow Corning), to reduce the possibility of the tube becoming permanently integral with balloon 14 during the bonding process, e.g., laser welding.

Next, balloon 14 is bonded to outer shaft 16. As shown in FIG. 4, laser energy (hv) can be used to bond or to weld balloon 14 to outer shaft 16. The laser energy is applied to balloon 14 and outer shaft 16 with sufficient energy to pass through tube including heat-shrink material 40, thereby thermally bonding the balloon to the outer shaft at the interface between the balloon and the outer shaft. Concurrently with applying the laser energy, a magnetic field (B) is applied to balloon 14 and outer shaft 16. As indicated above, during the bonding process, the polymeric material of balloon 14 and/or outer shaft 16 can become molten or partially molten, and consequently, the alignable material in the polymer material can move out of a desired alignment. By applying the magnetic field, the alignable material in the molten or partially molten polymer material can be maintained in the desired alignment (as shown, parallel to the longitudinal axis of the balloon). By keeping alignable material aligned and strengthening balloon 14, adverse effect(s) from laser bonding (such as formation of heat-affected zone that may weaken the balloon and/or its bond to outer shaft 16) can be reduced. Strengthening balloon 14 can be particularly desirable when the balloon is bonded to a portion of outer shaft 16 that has been thinned or necked to bond with the balloon. In other embodiments, the magnetic field can be applied to change the alignment of the alignable material from a first alignment (e.g., prior to bonding) to a second alignment different from the first alignment. The strength of the magnetic field applied can vary, as described above in the making of balloon 14. In other embodiments, the magnetic field and the laser energy are applied in the alternating manner. As another example, other methods of bonding components, such as RF welding, can be used.

Subsequent to bonding balloon 14 to the outer shaft 16, tube including heat-shrink material 40 can be removed from bonded balloon 14 and outer shaft 16 or kept in place, integral with the balloon catheter. For example, tube including heat-shrink material 40 can be removed by creating score lines that extend radially toward the center of the tube and longitudinally along the entire length or portions of the length of the tube. Scoring can make it easier and more controllable to remove tube including heat-shrink material 40 in embodiments in which removal is desirable.

While the above-described processes have been described with respect to outer shaft 16, in some embodiments, other components of balloon catheter 10 can alternatively or additionally be formed as described above with respect to outer shaft 16. As an example, referring to FIG. 1, distal waist portion of balloon 14 can be bonded to inner shaft 18 using the processes described above. As another example, FIG. 5 shows a rapid exchange or single-operator exchange balloon catheter 51 including an inner shaft 53, an outer shaft 55, and a balloon 57 bonded to the inner and outer shafts. Either or both shafts 53, 55 can include a mixture of a polymeric material and an alignable material. A soft distal tip 59 configured to fit coaxially over inner shaft 53 is also bonded to inner shaft 53 to provide a non-traumatic distal end. The proximal end of inner shaft 53 is bonded to outer shaft 55 near opening 61 at a location sometimes called a "port bond", which can be formed using the processes described herein. Similarly, distal tip 59 can include a mixture of a polymeric material and an alignable material and be bonded to inner shaft 53 using the processes described herein.

Other methods of making tubular members including a mixture of a polymeric material and an alignable material, such as the shafts described herein and distal tip 59, can also be used. For example, FIG. 6 shows an injection molding apparatus 63 including components 65 that engage together to form a cavity 67 and a port 69. Cavity 67 is sized according to a desired component, such as distal tip 59 or balloon 14. Port 69 is used to introduce a composite mixture of a polymeric material and an alignable material into cavity 67. To make a component, a liquid composite mixture of a polymeric material and an alignable material is introduced (e.g., injected) into cavity 67 via port 69. While the composite mixture is still liquid, a magnetic field (B) is applied and maintained along a predetermined direction to align the alignable material along the predetermined direction. When the composite mixture cools and solidifies, the alignable material is fixedly oriented along the predetermined direction.

Examples of magnetically alignable materials include carbon-containing materials (such as carbon single-walled nanotubes, carbon multi-walled nanotubes, and carbon fibers) and ferromagnetic materials. A ferromagnetic material has a magnetic susceptibility of at least about 0.075 when measured at 25° C., and can be, for example, a metal (e.g., a transition metal such as nickel, cobalt, or iron), a metal alloy (e.g., a nickel-iron alloy such as Mu-metal), a metal oxide (e.g., an iron oxide such as magnetite), a ceramic nanomaterial, a soft ferrite (e.g., nickel-zinc-iron), a magnet alloy (e.g., a rare earth magnet alloy such as a neodymium-iron-boron alloy or a samarium-cobalt alloy), an amorphous alloy (e.g., iron-silicon-boron), a non-earth alloy, or a silicon alloy (e.g., an iron-zirconium-copper-boron-silicon alloy, an iron-zirconium-copper-boron-silicon alloy). Magnetite is commercially available from FerroTec Corporation (Nashua, N.H.), under the trade name EMG 1111 Ferrofluid. Iron-copper-niobium-boron-silicon alloys are commercially available from Hitachi Metals of America under the trade name Finemet™. Iron-zirconium-copper-boron-silicon alloys are commercially available from MAGNETEC GmbH under the trade name Nanoperm®.

In certain embodiments, magnetically alignable fibers can have an average length of from about 50 nanometers to about 25 microns (e.g., from about 0.5 micron to about ten microns). Alternatively or additionally, magnetically alignable fibers can have an average width and/or diameter of from about 50 nanometers to about 25 microns (e.g., from about 0.5 micron to about ten microns). In some embodiments, the magnetically alignable material in a polymer composite can be a nanomaterial. Nanomaterials include particles and/or fibers having at least one dimension less than about 1000 nm.

In certain embodiments, magnetically alignable fibers can have an average aspect ratio of from about 1:1 to about 10:1 (e.g., from about 1:1 to about 5:1).

While magnetically alignable fibers have been shown, other forms of magnetically alignable material can be used in a polymer composite. For example, the magnetically alignable material can be in the form of particles, flakes, and/or a powder.

In some embodiments, the concentration of magnetically alignable fibers in the polymer composite stream can be from about two weight percent to about 50 weight percent (e.g., from about five weight percent to about ten weight percent).

Exemplary polymer matrix materials for a polymer composite material include thermoplastics and thermosets. Examples of thermoplastics include, for example, polyolefins; polyamides, such as nylon 12, nylon 11, nylon 6/12, nylon 6, and nylon 66; polyesters; polyethers; polyurethanes; polyureas; polyvinyls; polyacrylics; fluoropolymers; copolymers and block copolymers thereof, such as block copolymers of polyether and polyamide, e.g., Pebax® (e.g., Pebax® with a relatively high durometer value, such as 50); and mixtures thereof. Examples of thermosets include elastomers such as EPDM, epichlorohydrin, nitrile butadiene elastomers, silicones, etc. Conventional thermosets such as epoxies, isocyanates, etc., can also be used. Biocompatible thermosets, for example, biodegradable polycaprolactone, poly(dimethylsiloxane) containing polyurethanes and ureas, and polysiloxanes, may also be used. One or more of these materials can be used in the polymer composite material, in any combination.

Other polymer matrix materials include, for example, elastomers such as thermoplastic elastomers and engineering thermoplastic elastomers, such as polybutylene terephthalate-polyethene glycol block copolymers, which are available, for example, as HYTREL®. Elastomers are discussed, for example, in Hamilton U.S. Pat. No. 5,797,877, which is incorporated herein by reference in its entirety. Other polymers include liquid crystal polymers (LCP's). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)).

While a tubular member including a single polymer composite has been described, in some embodiments, a medical device can include at least one polymer composite and at least one polymer (e.g., a polymer that is substantially free of magnetically alignable material), or at least two different polymer composites.

Figure 7A:
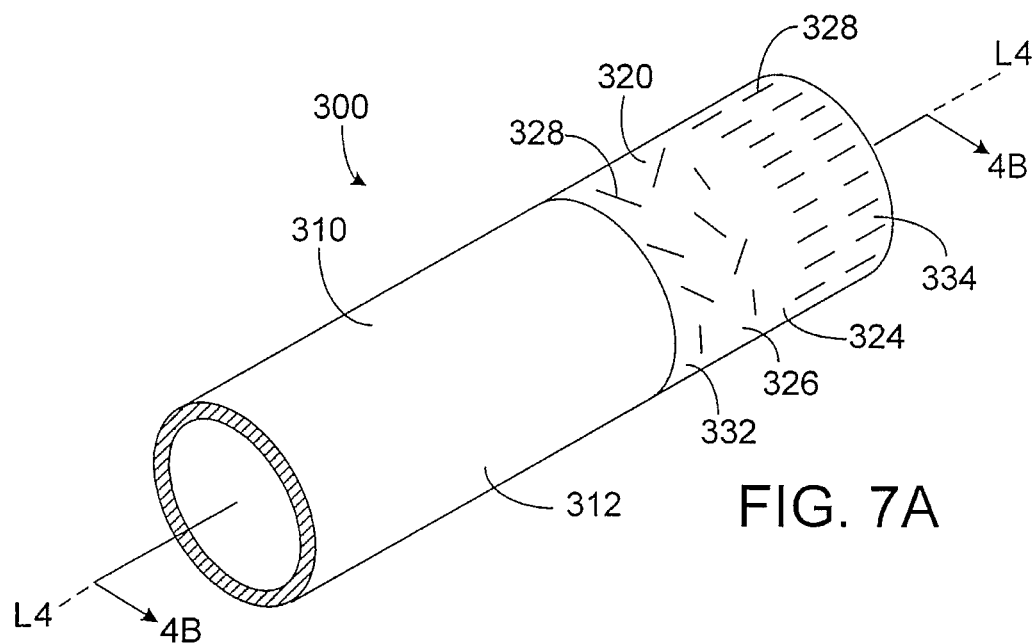
FIG. 7A is a perspective view of an embodiment of a tube for a balloon catheter system.
Figure 7B:
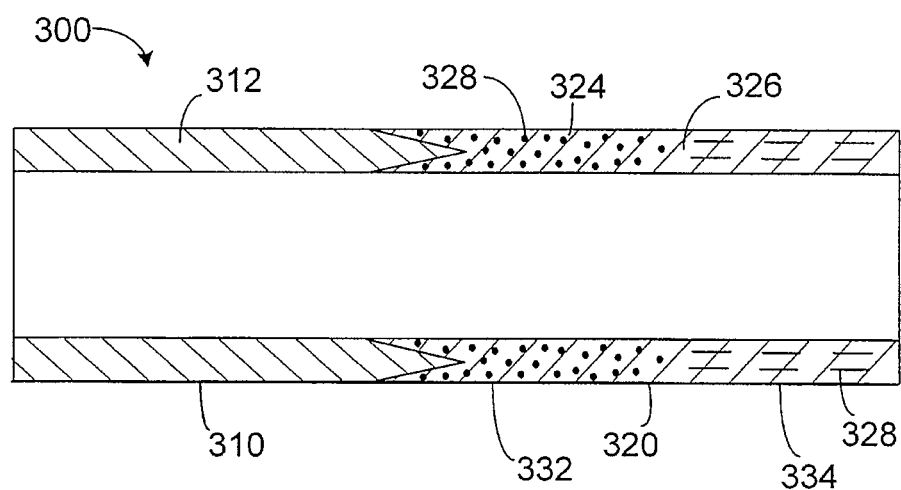
FIG. 7B is a cross-sectional side view of the tube of FIG. 7A, taken along line 4B-4B.

As an example, FIGS. 7A and 7B show a tubular member 300 that includes one section 310 formed of a polymer 312, and another section 320 formed of a polymer composite 324. Polymer composite 324 includes a polymer matrix 326 and magnetically alignable fibers 328. In region 332 of section 320, magnetically alignable fibers 328 have a random orientation, while in region 334 of section 320, magnetically alignable fibers 328 are aligned parallel to the longitudinal axis "L4" of tubular member 300. Polymer matrix 326 can be the same polymer as polymer 312, or can be different from polymer 312. Because of the presence of magnetically alignable fibers 328 in section 320, and the absence of magnetically alignable fibers 328 in section 310, section 320 has a higher magnetic permeability than section 310. In some embodiments, section 310 can have a magnetic permeability of from about one to about 20 (e.g., from about one to about seven). Alternatively or additionally, section 320 can have a magnetic permeability of from about five to about 30.

Figure 8A:
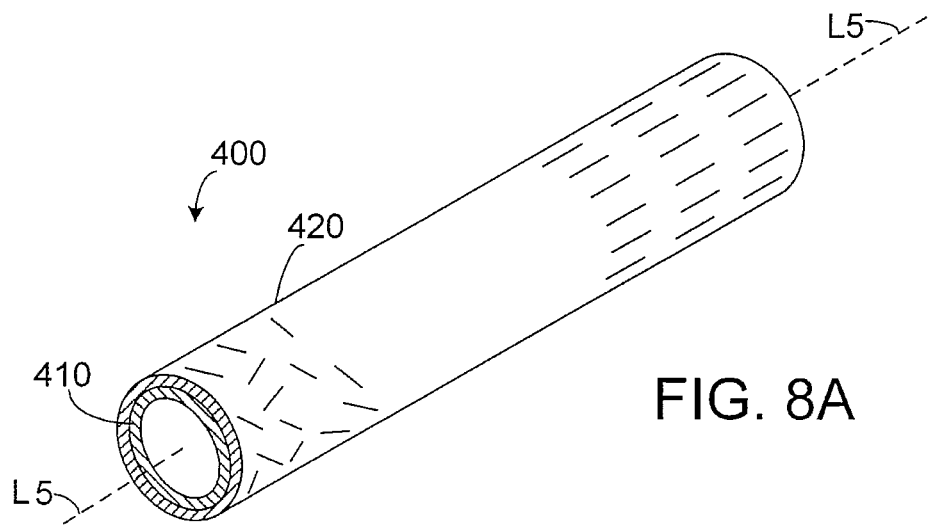
FIG. 8A is a perspective view of an embodiment of a tube for a balloon catheter system.
Figure 8B:
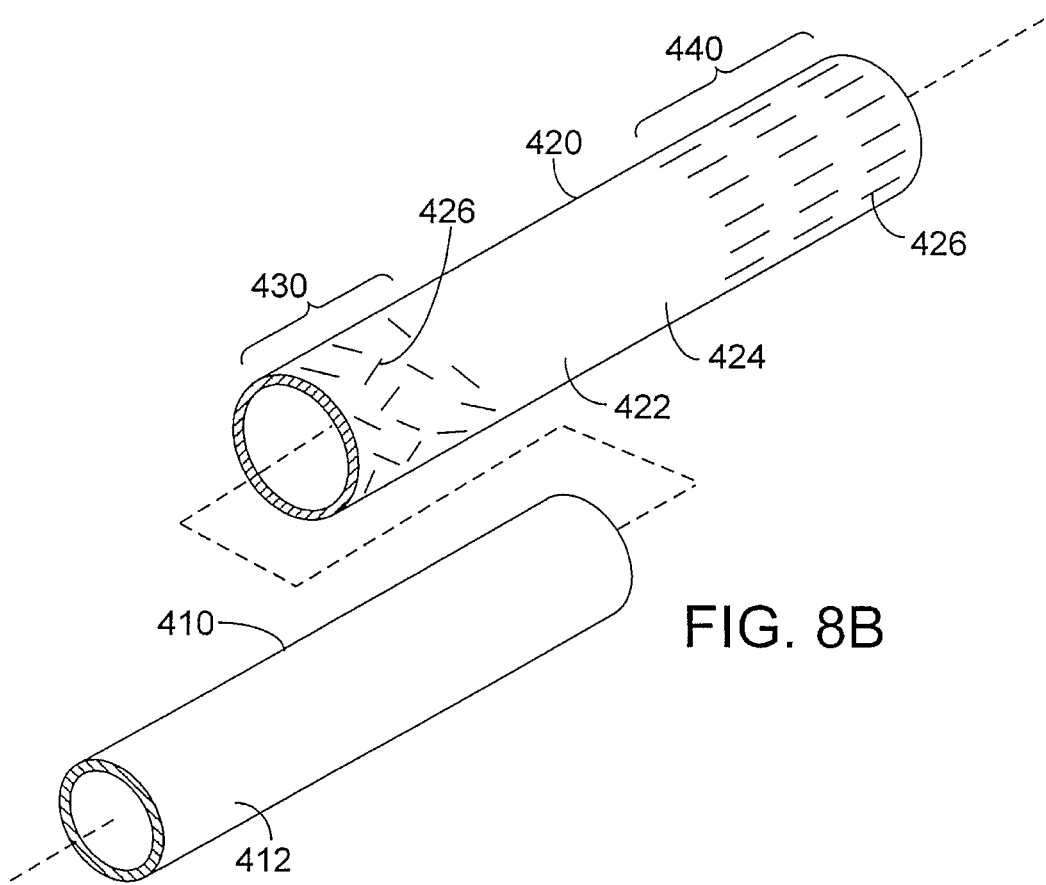
FIG. 8B is an exploded view of the tube of FIG. 5A.

As another example, in some embodiments, a tubular member can include more than one layer of material. For example, FIGS. 8A and 8B show a tubular member 400 that includes an inner layer 410 and an outer layer 420. Inner layer 410 includes a polymer 412, while outer layer 420 is formed of a polymer composite 422 that includes a polymer matrix 424 and magnetically alignable fibers 426. In region 430 of tubular member 400, magnetically alignable fibers 426 are randomly oriented, while in region 440 of tubular member 400, magnetically alignable fibers 426 are aligned parallel to the longitudinal axis "L5" of tubular member 400. In some embodiments, polymer matrix 424 of outer layer 420 can include a stiff polymer, so that the catheter system of which tubular member 400 is a part can be advanced through the body easily (e.g., without kinking or buckling). Alternatively or additionally, polymer 412 of inner layer 410 can be a polymer that gives inner layer 410 a smooth and lubricious inner surface (e.g., high density polyethylene), to, for example, ease passage of a guide wire through tubular member 400. While inner layer 410 is shown including polymer 412 and outer layer 420 is shown including polymer composite 422, a multilayer tubular member can include other arrangements of materials. As an example, a multilayer tubular member can have an inner layer that includes a polymer composite and an outer layer that includes a polymer. As another example, all of the layers of a multilayer tubular member can include a polymer composite. As a further example, a multilayer tubular member can have inner and outer layers that include a polymer composite, and an intermediate layer that includes a polymer.

Figure 9:
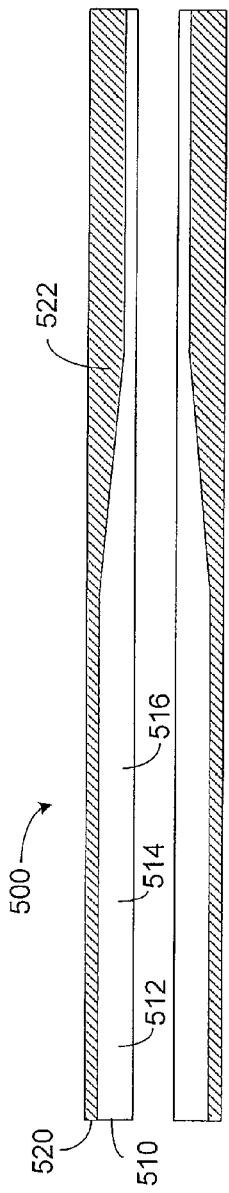
FIG. 9 is a cross-sectional side view of an embodiment of a tube for a balloon catheter system.

In some embodiments, the layers of material in a tubular member can have varying thicknesses. For example, FIG. 9 shows a cross-sectional view of a tubular member 500 that includes an inner layer 510 and an outer layer 520. Layers 510 and 520 have varying thicknesses along the length of tubular member 500. As shown, inner layer 510 includes a polymer composite 512 that includes a polymer 514 and magnetically alignable material 516, and outer layer 520 includes a polymer 522; in other embodiments, the locations of polymer composite 512 and polymer 522 can be reversed.

Figure 10:
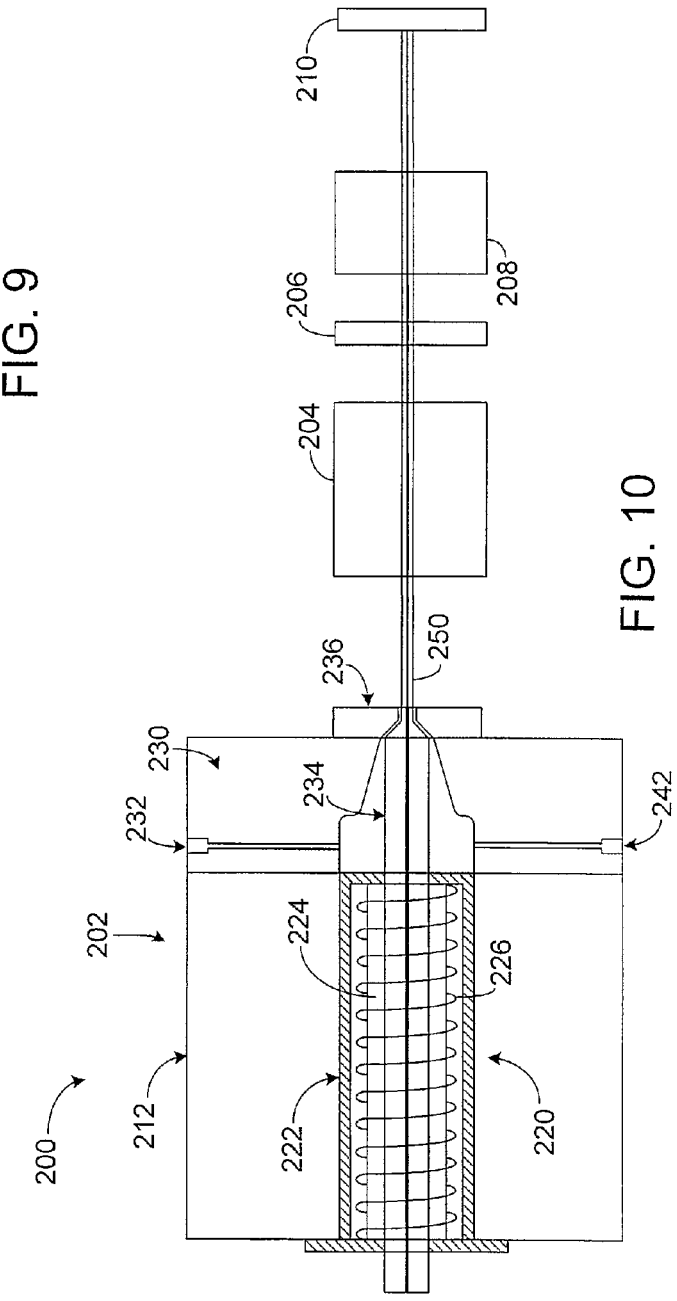
FIG. 10 is an illustration of an embodiment of an apparatus for making a tube for a balloon catheter system.

Tubular members (such as those shown in FIGS. 7A, 7B, 8A, 8B, and 9) that include two polymer composites or a polymer and a polymer composite can be formed, for example, using the tube-forming apparatus 200 shown in FIG. 10. Tube-forming apparatus 200 includes an extrusion head 202, a quench tank 204, a laser micrometer 206, a puller 208, and a cut-off knife 210. Extrusion head 202 has a housing 212 that encloses three sections of the extrusion head: a magnetic field-generating section 220 that includes a steel sleeve 222, an iron tip guide 224, and a coil 226 (e.g., a solenoid) between iron tip guide 224 and steel sleeve 222, a polymer feed section 230 that includes a first polymer feed 232, and an extrusion die 236. Hollow tip 234 passes through all three sections of extrusion head 202, and is in fluid communication with first polymer feed 232.

Polymer feed section 230 of apparatus 200 further includes a second polymer feed 242 that, like first polymer feed 232, is in fluid communication with tip 234. To form a tubular polymer member, a polymer is added into first polymer feed 232, and a polymer composite is added into second polymer feed 242. The polymer and polymer composite are melted to form liquid polymer and polymer composite streams that enter tip 234. The streams are then extruded through extrusion die 236, solidifying upon exposure to the ambient environment and thereby forming a tubular member 250. During the formation of tubular member 250, pressurized air (shown in FIG. 10 as a solid black line) flows through the center of hollow tip 234, causing the polymer and polymer composite streams to form a tubular shape (i.e., tubular member 250). In some embodiments, the polymer and polymer composite streams can be extruded using an intermittent extrusion process, such as the process described in Wang, U.S. Pat. No. 5,533,985, which is incorporated herein by reference in its entirety. In certain embodiments, the polymer and polymer composite streams can be extruded using a gradient extrusion process, such as the process described in Harris, U.S. Pat. No. 5,695,789, which is incorporated herein by reference in its entirety. Other methods are described, for example, in U.S. patent application Ser. No. 10/645,014, filed Aug. 21, 2003, and entitled "Multilayer Medical Devices"; WO 01/32398; and Burlis et al., U.S. Pat. No. 3,752,617.

The polymer composite stream that flows through extrusion apparatus 212 includes magnetically alignable material. During extrusion and formation of tubular member 250, the polymer composite stream can be exposed to a magnetic field that aligns the magnetically alignable material within the polymer composite stream. The magnetic field can be generated by activating coil 226 (by passing electrical current through the coil). Iron tip guide 224 propagates the magnetic field such that it is present along the length of hollow tip 234. Thus, the magnetic field affects the polymer composite stream as it flows through tip 234 and out through extrusion die 236.

Because tube-forming apparatus 200 includes two polymer feeds (232 and 242), tubular member 250 includes a section that is formed of a polymer and a section that is formed of a polymer composite. Each section can be in the form of a portion of tubular member 250 or a layer of tubular member 250.

Tubular member 300 of FIGS. 7A and 7B can be formed by deactivating coil 226 both during formation of section 310 and during formation of region 330 of section 320. The deactivation of coil 226 causes the magnetically alignable fibers in region 330 to be randomly oriented. However, coil 226 is activated when region 332 of section 320 is formed, such that the magnetically alignable fibers in region 320 are aligned parallel to the longitudinal axis "L2" of tubular member 300.

Tubular member 400 of FIGS. 8A and 8B can be formed by coextruding layers 410 and 420, deactivating coil 226 during the formation of section 430, and activating coil 226 during the formation of section 440. Similarly, tubular member 500 of FIG. 9 can be formed by coextruding layers 510 and 520, and activating or deactivating coil 226 according to the desired level of alignment of magnetically alignable material 516 in layer 510.

Materials other than polymers can be incorporated into an extrusion process during the formation of a multilayer tubular member. For example, an adhesion enhancing material can be incorporated into one or more material layers. An adhesion enhancing material can be used, for example, to enhance the adhesion between adjacent layers. Examples of adhesion enhancing materials include epoxy or anhydride modified polyolefins, such as LOTADER® (Atofina SA), KODAR® PETG (Eastman Kodak), and Plexar® (Equistar Chemicals LP). For example, in embodiments in which one layer includes high-density polyethylene and another layer includes Pebax®, a Plexar® layer can be included between the two layers to enhance adhesion. In some embodiments, an adhesion enhancing material can be added to a material (e.g., a composition containing one or more polymers) prior to extrusion. For example, in embodiments in which alternate layers are formed of PET and PBT, PETG can be added to the PET before extrusion.

In some embodiments, a compatibilizing material can be incorporated into one or more material layers. In certain embodiments, the compatibilizing material can enhance the compatibility between the layer(s) and one or more other layers in a multilayer medical device or medical device component. Examples of such compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl (meth)acrylate-ethylene-glycidyl (meth)acrylate polymers) can be used. Ionomeric copolymers can be used. PETG can be used. Examples of compatibilizing materials include HYTREL® HTR-6108, POLYBOND® 3009 (BP Chemicals), SP 2205 (Chevron), DS 1328/60 (Chevron), LOTADER® 2400, ESCOR® ATX-320, ESCOR® ATX-325, VAMAC® G1 and LOTADER® AX8660. In certain embodiments, a compatibilizing material (e.g., PETG) can be mixed with one or more polymers (e.g., an LCP-containing material) prior to extrusion.

In some embodiments, a compatibilizing material can be used to enhance the compatibility between the magnetically alignable material (e.g., magnetically alignable fibers) and one or more polymers in a medical device or medical device component. Examples of such compatibilizing materials include both organic and inorganic materials. Suitable organic compatibilizing materials can be both low molecular weight molecules and polymers. Examples of low molecular weight organic compatibilizing materials include, but are not limited to, amino acids (e.g., 12-aminododecanoic acid) and thiols. Examples of polymeric compatibilizers include functionalized polymers, such as maleic anhydride containing polyolefins or maleimide-functionalized polyamides. Inorganic compatibilizing materials can include, for example, alkoxides of silicon, aluminum, titanium, and zirconium.

Compatibilizing materials are further described, for example, in U.S. Published Patent Application No. 2003/0093107 A1, published on May 15, 2003, which is incorporated herein by reference.

Other Embodiments

While certain embodiments have been described, the invention is not so limited.

In some embodiments, the tubes and/or methods described herein can be used to form other medical devices or medical device components. Examples of medical devices include catheters (e.g., balloon catheters), balloons, guide wires, endoprosthesis delivery systems (e.g., stent delivery systems). Balloons are described, for example, in U.S. Published Patent Application No. 2004/0078052 A1, published Apr. 22, 2004, which is incorporated herein by reference. Guide wires are described, for example, in Wang et al., U.S. Pat. No. 6,436,056, which is incorporated herein by reference. Stent delivery systems are described, for example, in Raeder-Devens et al., U.S. Pat. No. 6,726,712, which is incorporated herein by reference. In some embodiments, the tubes and/or methods described herein can be used to form a dual lumen catheter with a shaft that includes multiple shaft sections and longitudinally extending lumens that are positioned side by side. Such catheters are described, for example, in Maguire et al., U.S. Pat. No. 4,782,834, which is incorporated herein by reference. In some embodiments, the above-described tubes and/or methods can be used in Intermittent Layer Coextrusion (ILC), which is described, for example, in Wang, U.S. Pat. No. 5,622,665; U.S. Ser. No. 10/645,014, filed on Aug. 21, 2004, and entitled "Multilayer Medical Devices"; U.S. Ser. No. 10/645,055, filed on Aug. 21, 2003, and entitled "Medical Balloons"; and U.S. Ser. No. 10/787,777, filed on Feb. 26, 2004, and entitled "Balloon Catheter", all of which are incorporated herein by reference in their entirety. In certain embodiments, the tubes described herein can have an enhanced ability to conduct low-voltage electricity and can be used, for example, in endoscopic applications.

Figure 11A:
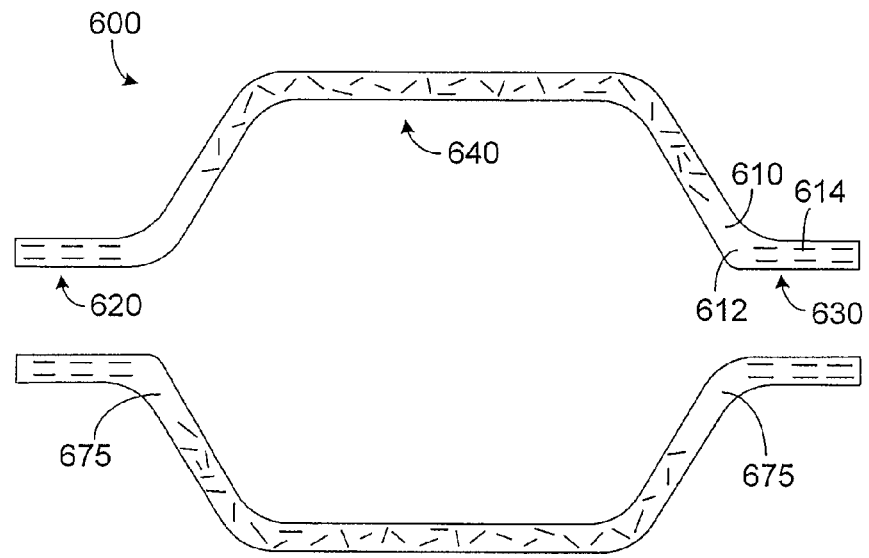
FIG. 11A is a cross-sectional side view of an embodiment of a balloon.

For example, and referring now to FIG. 11A, a tube formed by one of the above-described processes can be used to manufacture a medical balloon 600. Medical balloon 600 is formed of a polymer composite 610 that includes a polymer 612 and magnetically alignable fibers 614. As shown, fibers 614 are aligned at each of the waist sections 620 and 630 of balloon 600, and are randomly oriented at the expandable section 640 of balloon 600. However, in other embodiments, one or both of the waist sections of a balloon can include randomly oriented fibers, and/or the expandable section of a balloon can include aligned fibers. Also, while regions 675 of balloon 600 are shown as not including magnetically alignable material, in some embodiments, regions 675 can include magnetically alignable material (e.g., magnetically alignable fibers) that is aligned or randomly oriented, or that has an alignment that is between the alignment of fibers 614 at waist sections 620 and 630, and the random orientation of fibers 614 at expandable section 640.

Balloon 600 can be formed, for example, by a blow molding process in which a tube is placed (e.g., centered) in a preheated balloon mold, and air is introduced into the tube to maintain the patency of the tube lumen. In some embodiments, after being soaked at a predetermined temperature and time, the tube can be stretched for a predetermined distance at a predetermined time, rate, and temperature. The pressure inside the tube can then be sufficiently increased to radially expand the tube inside the mold to form the balloon. The formed balloon can be heat treated, for example, to enhance folding memory, and/or folded into a predetermined profile. The balloon can then be attached to a catheter to form a balloon catheter. Illustrative methods of forming a balloon from a tube are described in, for example, commonly-assigned U.S. patent application Ser. No. 10/263,225, filed Oct. 2, 2002, and entitled "Medical Balloon"; Anderson, U.S. Pat. No. 6,120,364; Wang, U.S. Pat. No. 5,714,110; and Noddin, U.S. Pat. No. 4,963,313, all of which are incorporated herein by reference in their entirety.

Figure 11B:
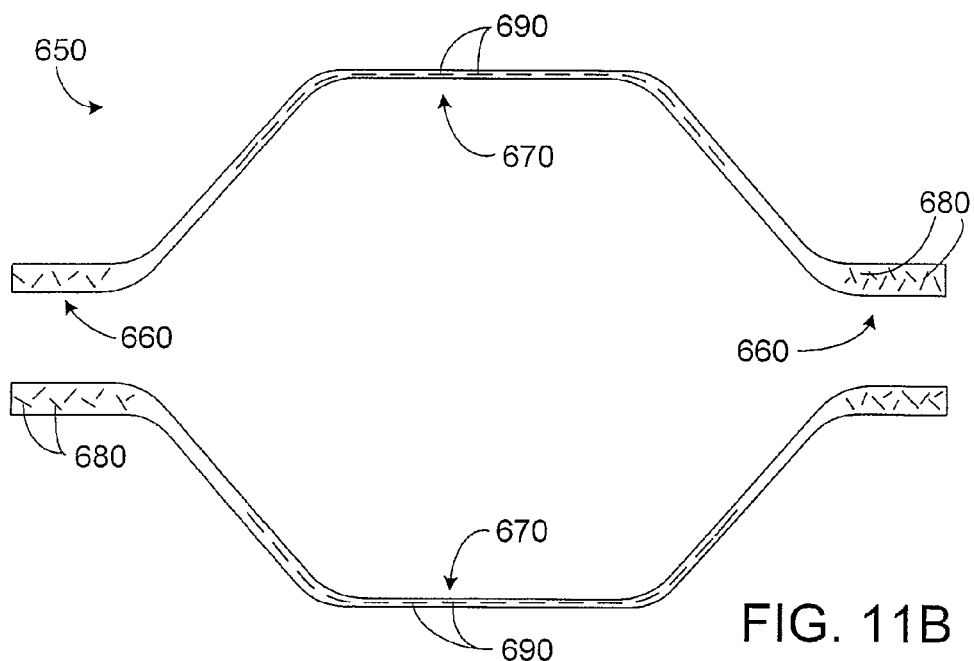
FIG. 11B is a cross-sectional side view of an embodiment of a balloon.

Referring now to FIG. 11B, in some embodiments, the molding of a balloon 650 can form relatively thick-walled waist regions 660, which can reduce the flexibility and trackability of the balloon. For example, during molding, the body portion 670 of the balloon can be stretched diametrically by at least a factor of six. As a result, the balloon wall in body portion 670 can be relatively thin because of the relatively large amount of stretching. However, portions of the balloon other than body portion 670, such as waist regions 660, may stretch relatively little (e.g., by a factor of approximately two). As a result, the portions of balloon 650 other than body portion 670 can remain relatively thick and can be inflexible. However, the addition of randomly oriented magnetically alignable fibers 680 to waist regions 660 can enhance the flexibility of the waist regions, while the addition of aligned magnetically alignable fibers 690 to body portion 670 can enhance the stiffness of body portion 670.

While not shown, in some embodiments, a balloon that includes magnetically alignable material can also include one or more cutting elements. Suitable materials for the cutting elements include, for example, stainless steel and plastic. Balloons with cutting elements are described, for example, in U.S. Published Patent Application No. 2003/0163148 A1, published on Aug. 28, 2003; U.S. Published Patent Application No. 2004/0133223 A1, published on Jul. 8, 2004; and U.S. Ser. No. 10/744,507, filed on Dec. 22, 2003, and entitled "Medical Device Systems", all of which are incorporated herein by reference.

As mentioned above, a tube formed according to one of the above-described processes can be formed into a guide wire, e.g., a polymer guide wire. Methods of making a guide wire, including one having good pushability, are described, for example, in U.S. Pat. No. 5,951,494, which is incorporated herein by reference in its entirety.

Figure 12:
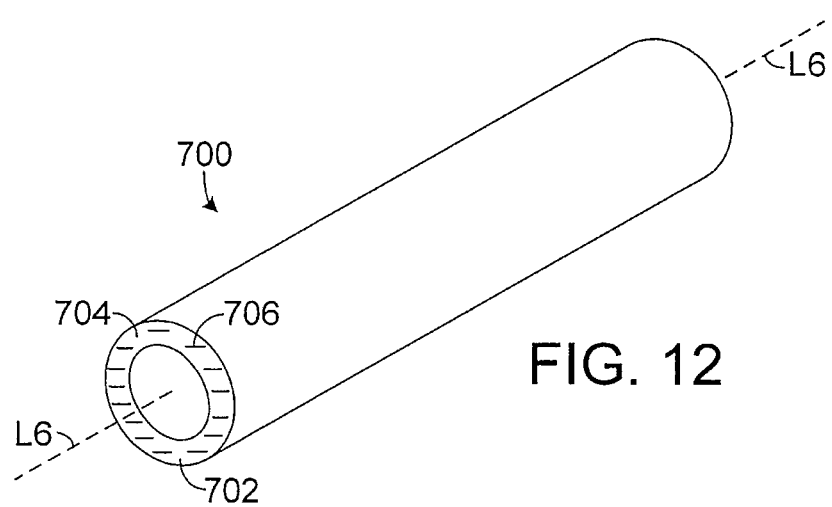
FIG. 12 is a perspective view of an embodiment of a tube for a balloon catheter system.

In certain embodiments, a tubular member can include magnetically alignable material that is aligned laterally relative to the longitudinal axis of the tubular member. For example, FIG. 12 shows a tubular member 700 formed of a polymer composite 702 that includes a polymer 704 and magnetically alignable fibers 706. Magnetically alignable fibers 706 are aligned laterally relative to the longitudinal axis "L6" of tubular member 700.

Figure 13A:
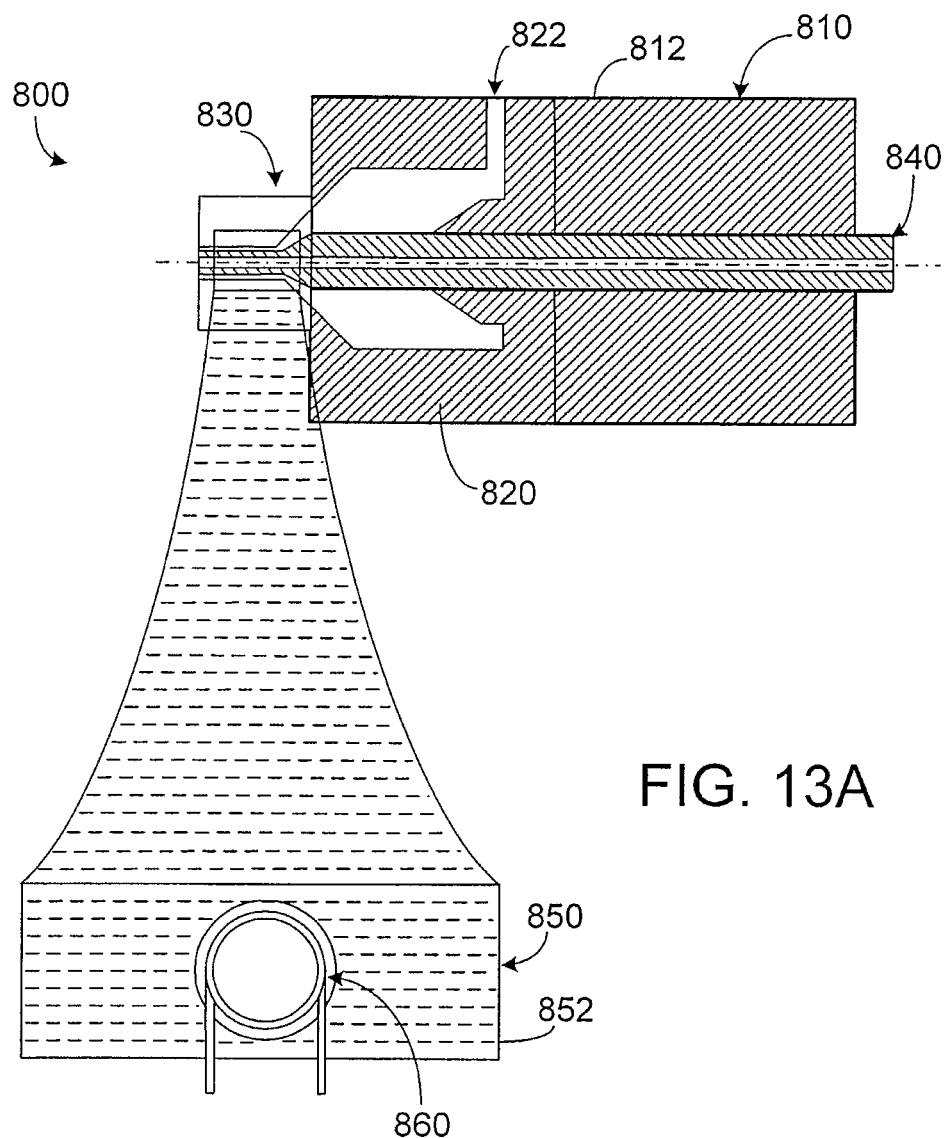
FIG. 13A is a side view of an embodiment of an apparatus for making a tube for a balloon catheter system.
Figure 13B:
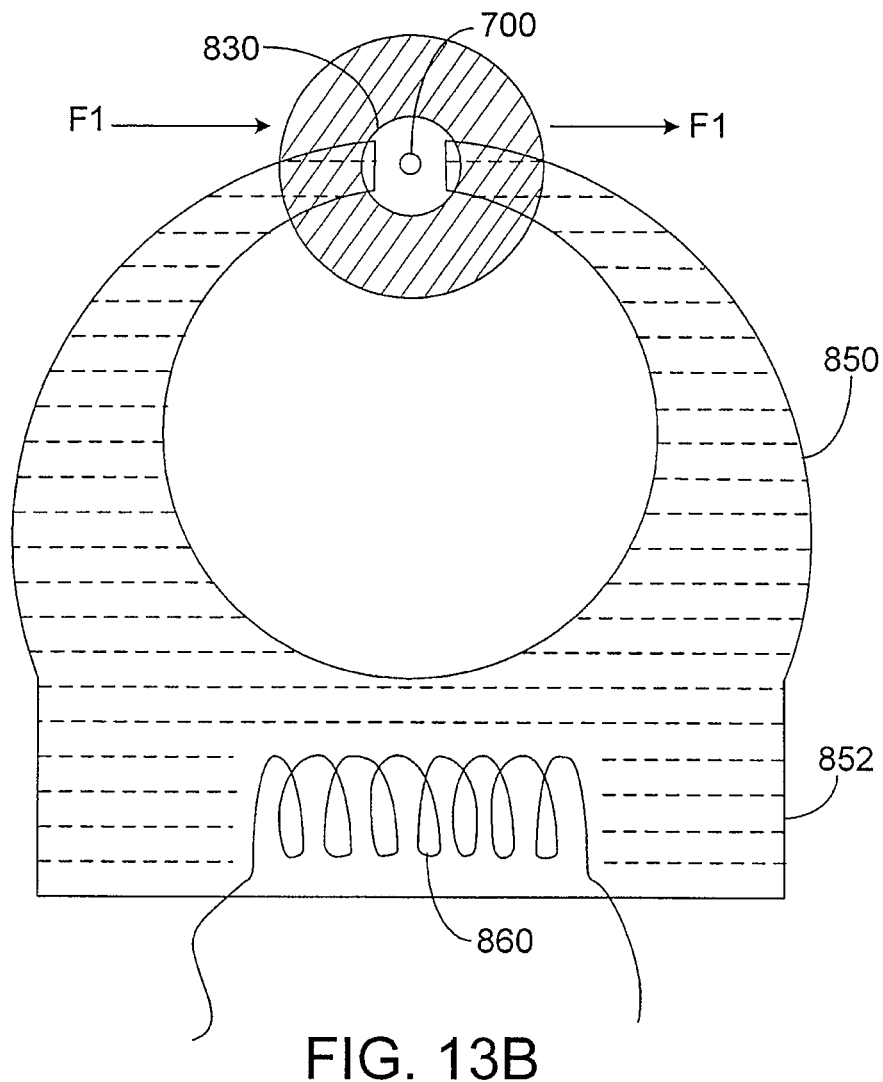
FIG. 13B is a front view of the apparatus of FIG. 13A.

Tubular member 700 can be formed, for example, using the tube-forming apparatus 800 shown in FIGS. 13A and 13B. Tube-forming apparatus 800 includes an extrusion head 810 with a housing 812 enclosing two sections: a polymer feed section 820 including a polymer feed 822, and an extrusion die 830. A hollow tip 840 extends through polymer feed section 820 and extrusion die 830, and is in fluid communication with polymer feed 822. Tubular member 700 can be formed similarly to the processes described above with reference to apparatus 90 of FIG. 3A and apparatus 200 of FIG. 10. However, tube-forming apparatus 800 generates a different type of magnetic field from the above-described apparatuses. As shown in FIGS. 13A and 13B, tube-forming apparatus 800 includes a magnet 850, in the bottom 852 of which is embedded a solenoid 860. When solenoid 860 is activated (by passing an electrical current through the solenoid), it generates a magnetic field that is propagated by magnet 850 to form a magnetic field force indicated by arrows F1. Thus, as the polymer composite stream exits extrusion die 830, it is exposed to a magnetic field that causes magnetically alignable fibers 706 to align laterally relative to tubular component 700.

In some embodiments, a medical device or medical device component can be formed by extruding a polymer composite through an extrusion head that includes a hollow tip and a magnetic mandrel disposed within the hollow tip. The magnetic mandrel can generate a magnetic field that aligns the magnetically alignable material within the polymer composite.

In certain embodiments, a tubular member can be formed by extruding a polymer composite while applying a varying magnetic field to the polymer composite. For example, a coil (e.g., a solenoid) can be activated (by passing an electrical current through the coil) to form a magnetic field. The magnetic field can be applied to the polymer composite as the polymer composite is being extruded. The magnetic field can be selectively reduced, increased, and/or deactivated as the polymer composite is being extruded, to vary the degree of alignment of the magnetically alignable material in the polymer composite.

In some embodiments, as a tubular member is extruded, the tubular member can be rotated relative to the longitudinal axis of the tubular member. The rotation of the tubular member as it is being extruded can, for example, further enhance the rotational or torsional stiffness of the tubular member. Extruded tubing formed by rotation during an extrusion process is described, for example, in Zdrahala, U.S. Pat. No. 5,238,305, and in U.S. Ser. No. 10/838,540, filed on May 4, 2004, and entitled "Medical Devices", both of which are incorporated herein by reference.

In some embodiments, a magnetic field can be applied to a polymer composite that includes a resin such as a thixotropic resin and, for example, nanotubes (e.g., carbon nanotubes, ceramic nanotubes). Without wishing to be bound by theory, it is believed that the magnetic field can cause the polymers of the thixotropic resin to orient themselves relative to the field, and to thereby indirectly orient the nanotubes by pulling the nanotubes along with them. In such embodiments, the magnetic field strength of the magnetic field that is applied to the polymer composite can be at least about ten Tesla (e.g., at least about 15 Tesla, at least about 20 Tesla) and/or at most about 25 Tesla (e.g., at most about 20 Tesla, at most about 15 Tesla). The orientation of carbon nanotubes in a polymer composite is described, for example, in Choi et al., "Enhancement of Thermal and Electrical Properties of Carbon Nanotube Polymer Composites by Magnetic Field Processing," 94 *Journal of Applied Physics* 9 (Nov. 1, 2003), 6034-6039, which is incorporated herein by reference in its entirety. Extrusion of nanocomposites is described, for example, in U.S. Ser. No. 10/728,079, filed on Dec. 4, 2003, and entitled "Medical Devices", which is incorporated herein by reference.

In certain embodiments, a polymer can be oriented by applying a magnetic field to magnetically alignable material (e.g., magnetically alignable fibers and/or particles) dispersed within the polymer. For example, a polymer composite that includes magnetically alignable fibers can be extruded to form a tubular member. As the middle portion of the tubular member is being formed, a magnetic field can be applied to the polymer composite to orient the magnetically alignable fibers in the middle portion with respect to the longitudinal axis of the tubular member. The orientation of the magnetically alignable fibers can cause the surrounding polymer to become oriented, as well. As the end portions of the tubular member are extruded, the magnetic field can be deactivated, such that the magnetically alignable fibers in the end portions do not become oriented with respect to the longitudinal axis of the tubular member, and thus do not orient the surrounding polymer. After the tube has been extruded, it can be formed into a balloon (e.g., as described above) having a relatively stiff body region (formed out of the middle portion of the tubular member), and relatively flexible waist regions (formed out of the end portions of the tubular member).

In certain embodiments, the above-described balloon can be subjected to stretching, which can have a different effect on different regions of the balloon. The stretching can cause the waist regions of the balloon to become relatively thin, but can have little to no effect on the thickness of the body region of the balloon. Thus, the balloon can be stretched in selected regions. As the thickness of the waist regions of the balloon decreases, the overall profile of the balloon during delivery also decreases, which can enhance the delivery of the balloon to a target site (e.g., by enhancing the pushability and/or trackability of the balloon).

In some embodiments, the above-described polymer orientation process can be used in combination with bump extrusion to produce a tubular member with areas of varying thickness and areas of varying orientation. For example, a tubular member can be formed with a relatively thick middle portion in which the polymer is oriented, and relatively thin end portions in which the polymer is not oriented. The tubular member can then be used, for example, to form a balloon having relatively thin and flexible waist regions, and a relatively thick and stiff body region. In certain embodiments, a balloon that has relatively thin and flexible waist regions, and a relatively thick and stiff body region, can have relatively good compatibility with a sheath of a delivery device such as a catheter. For example, the balloon may be easily wrapped around the delivery device (e.g., providing a lower profile for delivery) and inserted into and withdrawn from a sheath of the delivery device. The relatively low profile of the balloon can enhance the deliverability of the balloon, and can limit the likelihood of the balloon impeding the ability of the delivery device to, for example, cross a vascular lesion.

While a tube-forming apparatus with a coil (e.g., a solenoid) has been shown, in some embodiments other magnetic-field generating devices can be used. For example, a tube-forming apparatus can include a hele-shaw cell having magnetic parallel plates. Hele-shaw cells are described, for example, in Walker, "How to Build a Hele-Shaw Cell," excerpted from *Scientific American's The Amateur Scientist* (first published October 1989).

Figure 14:
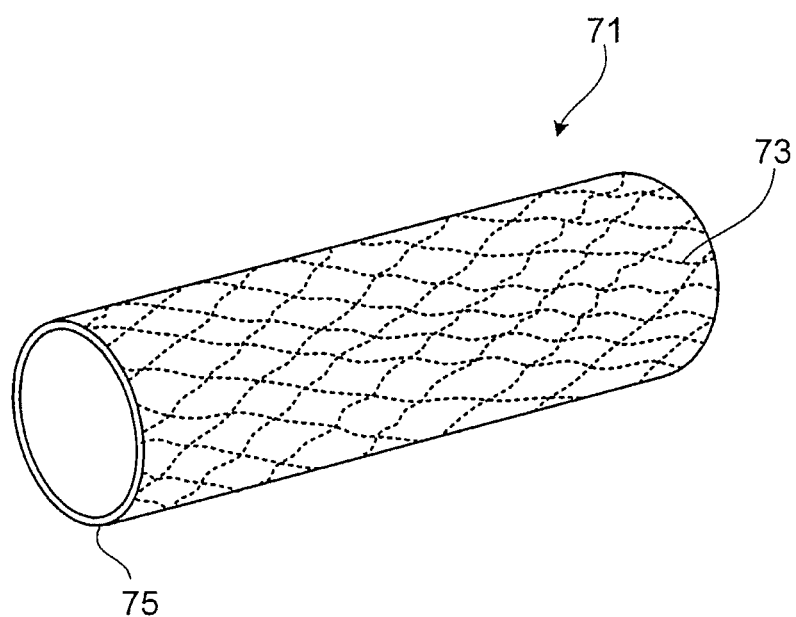
FIG. 14 is a perspective view of an embodiment of an endoprosthesis.

The methods of making tubular members described herein, such as extrusion and injection molding, can also be applied to make endoprostheses, such as stent-grafts and covered stents. Referring to FIG. 14, an endoprosthesis 71 includes a stent 73 including a metal or an alloy (such as stainless steel or a shape memory alloy (e.g., nickel-titanium)), and a tubular member 75 including a composite mixture of a polymeric material and an alignable material. Tubular member 75 can be on the exterior surface and/or the interior surface of stent 73. The composite mixture allows tubular member 75 to be made with reduced thickness without compromising the strength of the tubular member, or if maintained at the same thickness as a tubular member without the alignable material, further strengthen the tubular member. In some embodiments, tubular member 75 includes a bioerodible polymeric material and/or a therapeutic agent or drug, e.g., to reduce restenosis or thrombosis. Examples of bioerodible polymers include polyiminocarbonates, polycarbonates, polyarylates, polylactides, and polyglycolic esters. Examples of therapeutic agents include non-genetic therapeutic agents, genetic therapeutic agents, vectors for delivery of genetic therapeutic agents, cells, and therapeutic agents identified as candidates for vascular treatment regimens, for example, as agents targeting restenosis. Therapeutic agents are described, for example, in Weber, U.S. Patent Application Publication No. US 2005/0261760 A1, published on Nov. 24, 2005, and entitled "Medical Devices and Methods of Making the Same", and in Colen et al., U.S. Patent Application Publication No. US 2005/0192657 A1, published on Sep. 1, 2005, and entitled "Medical Devices".

The endoprosthesis can be made of a desired shape and size (e.g., coronary stents, aortic stents, peripheral vascular stents, gastrointestinal stents, urology stents, and neurology stents). Depending on the application, the endoprosthesis can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

The endoprostheses described herein can be configured for non-vascular lumens. For example, they can be configured for use in the esophagus or the prostate. Other lumens include biliary lumens, hepatic lumens, pancreatic lumens, urethral lumens and ureteral lumens.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. A method of manufacturing a medical device comprising:
   contacting a non-fluid first tubular member and a second tubular member, the first tubular member comprising a first polymer and an alignable material different from the first polymer;
   aligning the alignable material; and
   bonding the first and second members together concurrent with the step of aligning the alignable material.

2. The method of claim 1, wherein the alignable material is aligned magnetically.

3. The method of claim 1, wherein the alignable material comprises carbon.

4. The method of claim 3, wherein the alignable material comprises a carbon nanotube or a carbon fiber.

5. The method of claim 1, wherein the first member comprises from about 2 to about 50 percent by weight of the alignable material.

6. The method of claim 1, wherein the first and second members are held in contact by a heat shrink material.

7. The method of claim 1, wherein the first and second members are bonded by heating at least one of the members.

8. The method of claim 1, wherein the first and second members are bonded using a laser.

9. The method of claim 1, wherein the second member comprises a second polymer and a second alignable material.

10. The method of claim 1, wherein the fast and second members are components of a balloon catheter.

11. The method of claim 1, wherein the first member comprises from about 2 to about 60 percent by weight of the alignable material.

12. The method of claim 1, wherein the first member is solidified to form a component of a balloon catheter.

13. A method of manufacturing a tubular medical device or a medical device component having a longitudinal axis, the method comprising:
   introducing a first composition comprising a first polymer and an alignable material into a cavity;
   aligning the alignable material to have an orientation parallel to the longitudinal axis; and
   solidifying the first composition in the cavity.

14. The method of claim 13, wherein the alignable material is aligned magnetically.

15. The method of claim 13, wherein the alignable material comprises carbon.

16. The method of claim 15, wherein the alignable material comprises a carbon nanotube or a carbon fiber.

17. An endoprosthesis, comprising:
   a metallic tubular structure having a first end, a second end, a lumen extending from the first end to the second end and a longitudinal axis extending through the lumen from the first end to the second end; and
   a first composition on the tubular structure, the first composition comprising a polymer and an alignable material comprising a carbon nanotube or a carbon fiber aligned along a selected direction parallel the longitudinal axis.

18. The endoprosthesis of claim 17, wherein the first composition further comprises a drug.

19. The endoprosthesis of claim 17, wherein the first composition comprises from about 2 to about 50 percent by weight of the alignable material.

20. The method of claim 1 wherein only a portion of alignable material is aligned during the aligning step.

* * * * *

UNITED STATES PATENT AND TRADEMARK OFFICE
CERTIFICATE OF CORRECTION

PATENT NO. : 8,500,797 B2  
APPLICATION NO. : 12/119885  
DATED : August 6, 2013  
INVENTOR(S) : Olson et al.

Page 1 of 1

It is certified that error appears in the above-identified patent and that said Letters Patent is hereby corrected as shown below:

In the Claims

Column 20  
Claim 10, Line 14: delete "fast", and insert therefor -- first --.  
Claim 17, Line 43: after "direction parallel", insert -- to --.

Signed and Sealed this  
Third Day of June, 2014

Michelle K. Lee  
*Deputy Director of the United States Patent and Trademark Office*